United States Patent [19]

King

[11] Patent Number: 5,025,094

[45] Date of Patent: Jun. 18, 1991

[54] HETEROGENEOUS ALKOXYLATION USING ANION-BOUND METAL OXIDES

[75] Inventor: Stephen W. King, Charleston, W. Va.

[73] Assignee: Union Carbide Chemicals and Plastics Technology Corporation, Danbury, Conn.

[21] Appl. No.: 365,359

[22] Filed: Jun. 13, 1989

Related U.S. Application Data

[62] Division of Ser. No. 119,690, Nov. 12, 1987, Pat. No. 4,873,017, which is a division of Ser. No. 753,543, Jul. 10, 1985, Pat. No. 4,727,199.

[51] Int. Cl.⁵ .............................................. C07C 41/03
[52] U.S. Cl. .................................... 568/623; 568/613; 568/616; 568/624
[58] Field of Search ............... 568/606, 613, 620, 618, 568/622, 867, 623, 616, 624

[56] References Cited

U.S. PATENT DOCUMENTS

| | | | |
|---|---|---|---|
| 3,365,405 | 1/1968 | Fukui et al. | 260/2 |
| 4,112,231 | 9/1978 | Weibull et al. | 544/174 |
| 4,359,589 | 11/1982 | Brownscombe | 568/618 |
| 4,727,199 | 2/1988 | King | 568/620 |
| 4,814,515 | 3/1989 | Kumasaka et al. | 568/623 |
| 4,873,017 | 10/1989 | King | 252/183.11 |
| 4,886,917 | 12/1989 | Knopf et al. | 568/622 |

FOREIGN PATENT DOCUMENTS 103052 2/1938 Australia .
1185992 4/1985 Canada .

OTHER PUBLICATIONS

Hino, Makoto et al., J.C.S. Chem. Comm., 1980, pp. 851-852.
Hino, Makoto et al., Chemistry Letters, 1981, pp. 1671-1672.
Hino, Makoto et al., React. Kinet. Catal. Lett., vol. 19, No. 1-2, 1982, pp. 101-104.
Ohnishi, Ryuichiro et al., Zeitschrift fur Physikalische Chemie Neue Folge, vol. 130, S, 1982, pp. 205-209.
Chukhlantsev, V. G. et al., Russian Journal of Inorganic Chemistry, 18(6), 1973, pp. 770-771.
The Condensed Chemical Dictionary, 10th Ed., 1981, pp. 1115-1117.

*Primary Examiner*—Anthony McFarlane
*Attorney, Agent, or Firm*—Gerald L. Coon

[57] ABSTRACT

Active-hydrogen compounds, for example, primary and secondary alcohols or diols, are alkoxylated, for example, ethoxylated, using solid anion-bound metal oxide catalysts, such as, zirconium oxysulfate catalyst. Hydrous zirconium oxide is treated with solutions of sulfate phosphate, nitrate or tetrafluoroborate and calcined in air at 300° to 950° C. to produce highly active heterogeneous alkoxylation catalysts. The amorphous catalysts afford narrow molecular weight products. The catalyst can be removed from the product by filtration and reused with no significant loss in activity. Reaction temperatures of 50° to 140° C. are employed for alkoxylation.

12 Claims, No Drawings

HETEROGENEOUS ALKOXYLATION USING ANION-BOUND METAL OXIDES

This application is a division of prior U.S. application Ser. No. 119,690, filing date Nov. 12, 1987, now U.S. Pat. No. 4,873,017 which is a division of application Ser. No. 753,543, filing date July 10, 1985, now U.S. Pat. No. 4,727,199.

BACKGROUND OF THE INVENTION

1. Field of the Invention

The invention relates to a catalytic process of alkoxylating active-hydrogen compounds, to the starting compositions and to the alkoxylation catalysts.

2. Background Art

Hino, Makoto, and Kazushi Arata, "Synthesis of Solid Superacid Catalyst with Acid Strength of $H_0 < -16.04$", J. C. S. Chem. Comm., (1980) pages 851 and 852, discloses a solid superacid catalyst with an acid strength of $H_0 < -16.04$. The catalyst was obtained by exposing $Zr(OH)_4$, prepared by the hydrolysis of $ZrOCl_2$, to 1N $H_2SO_4$ and then calcining it in air at 575° to 650° C.

Hino, Makoto, and Kazushi Arata, "Synthesis Of Esters From Acetic Acid With Methanol, Ethanol, Propanol, Butanol, And Isobutyl Alcohol Catalyzed By Solid Superacid", Chemical Letters, Chem. Soc. Jap., (1981), pages 1671 and 1672, discloses catalytically esterifying acetic acid with lower alkanols, such as, ethanol. A solid superacid catalyst, which was obtained by exposing $Zr(OH)_4$ to 1N $H_2SO_4$ and then calcining in air at 500° to 750° C., was stated to be highly active for the heterogeneous esterification reactions at 30° to 45° C. The reactions with used catalysts gave identical results with those using freshly activated catalysts. (Esterification reactions are known to be catalyzed by acids.) Solid superacid catalysts were also prepared from Fe(OH)$_3$ and $H_4TiO_4$.

Hino, M., and K. Arata, "Conversion Of Pentane To Isopentane And Isopentane To Isobutane Catalyzed By A Solid Superacid In The Vapor Phase", React. Kinct. Catal. Lett., Vol. 19, No. 1-2, (1982), pages 101 to 104, discloses converting pentane and isopentane, respectively, into isopentane and isobutane using a solid superacid, which was prepared by exposing $Zr(OH)_4$ to 1N $H_2SO_4$, followed by calcination at 650° C. in air. The selectivities were 84 percent under short contact conditions at 80° C. The reactions involved the isomerization and hydrocracking of lower hydrocarbons. The paper states that Takahashi et al. prepared solid superacids by supporting $SbF_5$ on metal oxides and studied reactions of pentane and isopentane. [R. Ohnishi T., Morikawa, Y. Hiraga and K. Tanabe, Zeitschrift für Physikalische Chemic Nue Folg, Vol. 130, pp. 205-209, (1982)]

The above-discussed Hino and Arata articles are inconsistent and teach away from the invention which is the subject of this application.

Chukhlantsev, V. G., and Yu. M. Galkin, "Thermal Decomposition Of Basic Zirconium Sulphate", Russian Journal of Inorganic Chemistry, 18 (6), (1973), pages 770 and 771, earlier disclosed that when basic zirconium sulphate is heated to 500° to 650° C. (even above 400° to 420° C.) only dehydration, accompanied by the formation of an anhydrous product amorphous to X-rays, took place. Starting from 600° C. the latter decomposed with the formation of $ZrO_2$ and release of $SO_3$. Basic zirconium sulfate was obtained by boiling a solution of zirconium oxide chloride containing 50 g of $ZrO_2$ per liter, 15 g of free HCl per liter, and sulfuric acid to give $SO_3$: $ZrO_2 = 0.56$ (molar). The product was washed and then dried at 100° C.

The Condensed Dictionary, 10th Ed., (1981) pages 1115 to 1117, discloses: $Zr_5O_8(SO_4)_2.xH_2O$, zirconyl sulfate on zirconium sulfate, basic; $ZrOCO_3.xH_2O$, zirconyl carbonate or zirconium carbonate, basic; $ZrOCl_2.8H_2O$, zirconyl chloride or zirconium oxychloride; $ZrO(OH)Cl._nH_2O$, zirconyl hydroxychloride; and $ZrO(OH)NO_3$, zirconyl hydroxynitrate or zirconyl nitrate, basic. Zirconium oxychloride can be prepared by the action of hydrochloric acid on zirconium oxide. Zirconyl sulfate can be prepared in a similar manner. $Zr(OH)_4$ can be prepared by the action of a solution of sodium hydroxide on a solution of a zirconium salt.

Ethylene oxide, also termed oxirane, has been reacted with $C_2H_5OH$ to produce $C_2H_5OCH_2CH_2OH$. The same reaction with ethylene sulfide is known.

BROAD DESCRIPTION OF THE INVENTION

The invention involves the basic and unexpected discovery that anion-bound zirconium oxides and certain other anion-bound metal oxides are heterogeneous catalysts for alkoxylation, particularly ethoxylation. The invention process is broadly the use of anion-bound metal oxide heterogeneous catalysts for the alkoxylation of active-hydrogen compounds, such as, primary or secondary alcohols and diols: Anion-bound zirconium oxide heterogeneous catalysts are highly active.

The invention process for the alkoxylation of active-hydrogen compounds includes reacting a liquid or solid reactive epoxide compound having the formula:

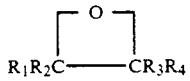

wherein $R_1$, $R_2$, $R_3$ and $R_4$ are each H or $-(CH_2)_nCH_3$, and wherein n is 0 to 3, with the proviso that $R_1$, $R_2$, $R_3$ and $R_4$ can be the same or different, with an active-hydrogen compound, the active-hydrogen compound being in the liquid or gaseous state, in the presence of a catalytic amount of at least one solid anion-bound metal oxide catalyst. The anion-bound metal oxide catalyst is an amorphous or primarily amorphous compound. The active-hydrogen compound is one which does not poison the catalyst. The preferred active-hydrogen compound is preferably a primary monohydric alcohol, a secondary monohydric alcohol, a dihydric alcohol, a trihydric alcohol, a polyhydric alcohol, an alkoxylated ethylene glycol or a glycol ether. Water can be used as the active hydrogen compound. The molar ratio of the cyclic epoxide compound to the active-hydrogen compound is usually between 3:1 and 1:3. The process is especially advantageous in the ethoxylation of ethylene glycol.

In the processes of the invention, the preferred epoxide compound is ethylene oxide. Also preferably the reaction is continuously conducted in a fixed-bed reactor or a fluidized reactor. Also in the processes of the invention, preferably 0.5 to 50 weight percent, based on the total weight of the cyclic epoxide compound and the other reactant or reactants, of the solid anion-bound metal oxide catalyst is used. Preferably the anion in the anion-bound metal oxide catalyst is $SO_4$, $BF_4$, $CO_3$, $BO_3$, $HPO_4$, $SeO_4$, $MoO_4$, $B_4O_7$ or $PF_6$, and the metal oxide in the anion-bound metal oxide catalyst is zirconium oxide, nickel oxide, aluminum oxide, tin oxide, magnesium oxide, rubidium oxide, titanium oxide, thorium oxide, hafnium oxide or iron oxide. ZrO will readily bind with anions other than $SO_4$; whereas the other metal oxides will readily bind with $SO_4$ but not as readily with the other anions. Preferably the catalyst is a solid sulfate-bound zirconium oxide catalyst, a solid sulfate-bound thorium oxide catalyst or a solid sulfate-bound hafnium oxide catalyst. Although not preferred, the reactants can be used in inert liquid diluents such as hydrocarbons. Normally, the catalyst can be reused with good selectivity. If necessary, the solid anion-bound metal oxide catalyst can be removed from the reaction site and can be regenerated by calcination in air or oxygen at a temperature of 300° to 950° C. for a period of 1 to 4 hours.

An advantage of the invention process is that it produces a narrow molecular range of products with a minimum of undesirable high molecular weight coproducts or by-products.

The polyoxyethylation of an alcohol is a process of reacting an alcohol with ethylene oxide to produce a polyether, as in the reaction below, in which R of the alcohol can be aliphatic or aromatic:

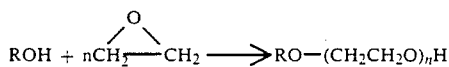

The number of moles (n) of ethylene oxide reacted can range from 1 to greater than 200. The reaction occurs by a stepwise addition of the polymerization process usually catalyzed by acids or bases. The average molecular weight of the product alcohols is determined by the moles of ethylene oxide reacted compared to the moles of hydroxyl groups in the starting alcohol. The product can contain significant amounts of unreacted starting alcohol, depending on the relative reactivity of the starting alcohol compared to the reactivity of the product alcohols. All unhindered hydroxyl groups of monohydric and polyhydric alcohols react, but some may be more reactive than others. The process temperatures usually range from 80° to 180° C. with the pressure at a level (e.g., 20 to 100 p.s.i.g.) needed to maintain conditions in the reactor. Often an excess of alcohol and/or cyclic epoxide is used.

The invention also involves a composition containing (a) a liquid or solid epoxide compound having the formula:

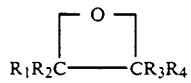

wherein $R_1$, $R_2$, $R_3$ and $R_4$ are each H or $-(CH_2)_n CH_3$, and wherein n is 0 to 3, with the proviso that $R_1$, $R_2$, $R_3$ and $R_4$ can be the same or different, (b) an active-hydrogen compound, such as, a secondary monohydric alcohol, a dihydric alcohol, a trihydric alcohol, a polyhydric alcohol, an alkoxylated ethylene glycol or a glycol ether, the active-hydrogen compound being in the gaseous or liquid state, and (c) a catalytic amount of at least one solid anion-bound metal oxide catalyst. The anion-bound metal oxide catalyst is an amorphous or primarily amorphous compound. The active-hydrogen compound is one which does not poison the catalyst.

The invention further involves reacting at least one molecule of a liquid or solid epoxide compound having the formula:

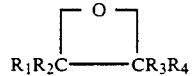

wherein $R_1$, $R_2$, $R_3$ and $R_4$ are each H or $-(CH_2)_n CH_3$, and wherein n is 0 to 3, with the proviso that $R_1$, $R_2$, $R_3$ and $R_4$ can be the same or different, with at least one other molecule of the above-identified liquid or solid epoxide compound in the presence of a catalytic amount of at least one solid anion-bound metal oxide catalyst. The molecules of epoxide compound can be the same epoxide compound or different epoxide compouds. The anion-bound metal oxide catalyst is an amorphous or primarily amorphous compound.

The invention still further involves a composition including (a) at least one liquid or gaseous epoxide compound having the formula:

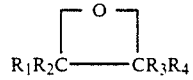

wherein $R_1$, $R_2$, $R_3$ and $R_4$ are each H or $-(CH_2)_n CH_3$, and wherein n is 0 to 3, with the proviso that $R_1$, $R_2$, $R_3$ and $R_4$ can be the same or different, and (b) a catalytic amount of at least one solid anion-bound metal oxide catalyst. The anion-bound metal oxide catalyst is an amorphous or primarily amorphous compound.

The invention also involves the alkoxylation process of reacting an epoxide compound having the formula:

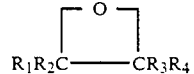

wherein $R_1$, $R_2$, $R_3$ and $R_4$ are each H or $-(CH_2)_n CH_3$, and wherein n is 0 to 3, with the proviso that $R_1$, $R_2$, $R_3$ and $R_4$ can be the same or different, with a sodium salt of an acid sulfate of a secondary monohydric alcohol having 10 to 20 carbon atoms, the secondary monohydric alcohol salt being in the liquid state, in the presence of a catalytic amount of at least one solid anion-bound metal oxide catalyst. The anion-bound metal oxide catalyst is an amorphous or primarily amorphous compound. The molar ratio of the epoxide compound and the secondary monohydric alcohol salt is usually between 3:1 and 1:3.

The invention further involves the composition comprised of (a) a liquid or gaseous epoxide compound having the formula:

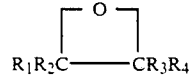

wherein $R_1$, $R_2$, $R_3$ and $R_4$ are each H or $-(CH_2)_n CH_3$, and wherein n is 0 to 3, with the proviso that $R_1$, $R_2$, $R_3$ and $R_4$ can be the same or different, (b) a sodium salt of an acid sulfate of a secondary monohydric alcohol having 10 to 20 carbon atoms, the secondary monohydric alcohol salt being in the liquid state, and (c) a catalytic amount of at least one solid anion-bound metal oxide catalyst. The anion-bound metal oxide catalyst is an amorphous or primarily amorphous compound. The molar ratio of the epoxide compound and the secondary monohydric alcohol salt is usually between 3:1 and 1:3.

Another important aspect of the invention is that it encompasses solid anion-bound metal oxide catalysts which are: (a) sulfate-bound tin oxide catalyst, (b) sulfate-bound nickel oxide catalyst, (c) sulfate-bound aluminum oxide catalyst, (d) sulfate-bound magnesium oxide catalyst, (e) sulfate-bound rubidium oxide catalyst, (f) sulfate-bound thorium oxide catalyst, (g) sulfate-bound hafnium oxide catalyst, or (h) an anion-bound metal oxide catalyst wherein the anion is $SO_4$, $BF_4$, $CO_3$, $HPO_4$, $SeO_4$, $MoO_4$, $B_4O_7$ or $PF_6$, and the metal oxide is an oxide of zirconium, nickel, aluminum, tin, magnesium, iron, titanium, thorium, hafnium or rubidium. The anion-bound metal oxide catalyst is an amorphous or primarily amorphous catalyst. The catalysts are useful in the above-described alkoxylation processes and in the processes set out in the above prior art section.

DETAILED DESCRIPTION OF THE INVENTION

As used herein, all parts, ratios, percentages and proportions are on a weight basis unless otherwise stated herein or otherwise obvious herefrom to one skilled in the art.

The anion-bound metal oxide catalysts of the invention are heterogeneous catalysts, that is, they are useful in heterogeneous catalysis. Heterogeneous catalysis involves a catalytic reaction in which the reactants and the catalyst comprises two separate phases, e.g., gases over solids, or liquids containing finely-divided solids as a disperse phase. (By way of contrast, homogeneous catalysis involves a catalytic reaction in which the reactants and the catalyst comprise only one phase, e.g., an acid solution catalyzing other liquid components.) The subject alkoxylation reactions of the invention occur on the surface of the solid catalyst particles. The individual steps of heterogeneous catalytic processes probably involve the following:
(1) Diffusion of reactants to surface.
(2) Adsorption of reactants on surface.
(3) Reaction of absorbed reactant to form adsorbed product.
(4) Desorption of product.
(5) Diffusion of product into main stream of a liquid or vapor.

The reaction rates of alkoxylation reactions were unexpectedly significantly increased by the solid anion-bound metal oxide catalysts of the invention.

While a catalytic amount of catalyst is to be used, preferably 0.5 to 50 weight percent of the catalyst is used based on the total weight of the reactants. Of course, higher levels of the catalyst can be used and mixtures of the catalysts can be used. One or more promoters can also be used.

One of the preferred anion-bound metal oxide catalysts is zirconium oxysulfate catalyst. It provides a substantial increase of reaction rate in ethoxylations with excellent selectivity. For example, the use of zirconium oxysulfate catalyst in the ethoxylation of ethylene glycol produces very little of the undesirable 1,4-dioxane.

Production of the catalyst involves, for example, reacting a compound having an anion with the metal hydroxide, such as, $Zr(OH)_4$, $Zr(OH)_4.xH_2O$, $Hf(OH)_4$, $Fe(OH)_3$, $Al(OH)_3$, $Th(OH)_4$, $Ni(OH)_2$, and $Mg(OH)_2$. (Any other suitable method can be used to prepare the catalyst.)

The metal hydroxide can be produced by hydrolyzing metal oxy-anion group compounds, such as, $ZrOCl_2.8H_2O$, $ZrO(NO_3)_2.2H_2O$, $Zr_5O_8(SO_4).xH_2O$, $ZrO(C_2H_3O_2)_2$, $ZrOBr_2.xH_2O$, $ZrOI_2.8H_2O$, $ZrO_5$, $HfOCl_3.8H_2O$, $ZrOOHCl._nH_2O$, $ZrO(OH)NO_3$ and $ZrO(SO_4)$. The hydrolysis can be achieved using a hydrolyzing agent, such as, ammonium hydroxide, sodium hydroxide, potassium hydroxide, barium hydroxide, lithium hydroxide, magnesium hydroxide, $Na_2SO_4$, $(NH_4)_2HPO_4$ and so forth. Following hydrolysis, the solids are removed from the hydrolysis solution, usually by filtration, dried (at say 100° C. or any other appropriate temperatures) and optionally particulated or powdered.

The metal hydroxide is treated with the reactive compound containing an anionic group under suitable conditions. The anion can be monovalent or divalent or have a higher valence. Examples of the reactive compounds having an anionic group are $H_2SO_4$, phosphoric acid, nitric acid, etc. Such acids are examples of the reactive compounds having an anionic group, but Lewis acids can also be used as such reactive compounds having an anionic group. A Lewis acid is a substance that can act as an electron-pair acceptor. Lewis acids include trivalent derivatives of boron and aluminum, as well as salts of many other metals. Examples of specific Lewis acids are $BF_3$, $BCl_3$, $AlCl_3$, $AlF_3$, $FeCl_3$, $SnCl_4$, $ZnCl_2$, $LiCl$, $MgCl_2$, $AlH_3$, $PF_5$, $SbF_5$ and $SO_3$.

If one starts with compounds such as $ZrOSO_4$ and $TiOSO_4$, the sulfate-bound metal oxide compounds can be prepared directly by adding the hydrolyzing agent (e.g., sodium hydroxide) to a solution of the $ZrOSO_4$, $TiOSO_4$ or the like.

The solid anion-bound metal oxide catalyst is normally dried (at 100° C. or any other suitable temperature) before being calcined. The drying step to be used is any technique which sufficiently evaporates the volatile constituents of the impregnating solution.

Calcination of the anion-bound metal oxide catalyst can be done in air or oxygen at a temperature of 300° to 950° C., preferably 500° to 800° C., for a suitable period of time. The calcination is normally conducted for one to four hours, or more. Zirconium oxysulfate catalyst production preferably involves calcination in air at a temperature of about 575° C.

The calcined catalyst has its water molecules removed by the calcination, so the calcined catalyst should be kept in an air-tight container, such as, a desiccator, until it is used.

The zirconium catalysts of the invention are not zirconyl salts, such as, zirconium oxysulfate. Instead, the zirconium catalysts of the invention are anion-bound zirconium oxides. The anion, for example, $SO_4$, bridges the zirconium oxide moieties. Examples of such anions are $SO_4$, $BF_4$, $CO_3$, $BO_3$, $HPO_4$, $SeO_4$, $MoO_4$, $B_4O_7$ or $PF_6$, and the metal oxide is zirconium, nickel, aluminum, tin, magnesium, iron, titanium, thorium, hafnium or rubidium. Metal oxides of Group IVB metals are most preferred. The anion bound to the metal oxide in the catalysts can be inorganic anions and/or organic anions. Inorganic anionic groups are preferred, with the sulfate group being the most preferred.

Other anion-bound oxide catalysts can be used in place of anion-bound zirconium oxide catalyst, although the anion-bound zirconium oxide catalyst is most preferred. Examples of other anion-bound metal oxides are anion-bound iron oxide (preferred), anion-bound aluminum oxide, anion-bound nickel oxide, anion-bound tin oxide, anion-bound magnesium oxide, anion-bound rubidium oxide, anion-bound titanium oxide (preferred), anion-bound thorium oxide (most preferred), and anion-bound hafnium oxide (most preferred). Thorium oxide catalysts may be more advantageous than zirconium oxide catalysts since they are very insoluble and thorium is not amphoteric like zirconium. Amphoteric means acting as either an acid or base. Experimentation has found that anion-bound cerium oxide, anion-bound lanthanum oxide, anion-bound tungsten oxide and certain other anion-bound metals do not work as catalysts in the invention process of catalytically alkoxylating certain compounds. This lack of catalytic activity of certain anion-bound metal oxides shows the unexpected nature of the invention.

The metal oxides used in the anion-bound metal oxide catalysts are amorphous or used in amorphous form. For example, one uses the amorphous forms of alumina as opposed to the crystalline forms of alumina. The metal oxides can also be primarily or mainly amorphous, that is, more of the metal oxide is in the amorphous state than in the crystalline state. The crystalline forming metal oxides, such as, calcium oxide, are not used.

Only solid, insoluble catalysts are used so that a heterogeneous catalytic reaction is involved. Catalysts based on K, Ba and Na are soluble in the reactants and/or product and/or diluent, so they are not used in the invention.

1,4-dioxane or 1,4-diethylene dioxide is undesirable, but is produced to a small extent by all of the invention catalysts. The anion in the catalyst needs to be bound totally or else it leaches into the reaction medium and increases the acidity with the resultant production of dioxane. Preferably 2 to 3 weight percent of the anion (e.g., SO$_4$) is bound to the metal oxide. The use of Na$_2$SO$_4$ in place of H$_2$SO$_4$ eliminates the minor dioxane production caused by the latter, but Na$_2$SO$_4$ causes a slower reaction rate. In general, the more basic the anion-bound metal oxide catalyst is, the less the amount of dioxane that is produced.

The anion-bound metal oxide catalyst is usually used in a finely-divided particulate state. Mixtures of anion-bound metal oxide catalysts can be used.

Carriers or supports can be used to support the anion-bound metal oxide catalyst. The support is used in a particulate form and can be porous or nonporous, although the former is preferred. Usually the support particles have diameters between 1 and 5 mm. Preferably, carriers are used which are inert to the reactants and products of the subject alkoxylation reactions.

The preferred carriers are silica gel and 4 A alumina-silica sieves. Examples of other useful inert carriers are diatomaceous earth, silica, alumina (e.g., α-alumina), silica-alumina, calcined clays, charcoal and zeolites.

The catalysts can even be used in a porous, unsupported form.

The anion-bound metal oxide catalysts can be regenerated or reactivated by calcination, for example. Zirconium oxysulfate catalyst is preferably regenerated by calcination in air at a temperature of about 575° C. Generally regeneration calcination is run in air or oxygen at a temperature between 300° and 950° C., preferably between 500° and 800° C., for a period of time which is usually one to four hours, or more.

Generally the recovered catalyst does not have to be regenerated and can be used as is with no loss of selectivity.

The reactants within the scope of the invention are in the gaseous and/or liquid state, although a reactant could be used in the solid state if it was in a finely-divided particulate form, for example, suspended in a liquid carrier (diluent) or a different liquid reactant. Solid reactants can also be used if they are dissolved in a liquid solvent. The anion-bound metal oxide catalyst is used in a solid form.

Examples of liquid nonpolar diluents from which the appropriate diluent can be selected are: acetic acid nitrile, anthracene, benzene, chlorobenzene, 1,2-dichlorobenzene, ethylbenzene, isopropylbenzene, 1-isopropyl-4-methylbenzene, nitrobenzene, propylbenzene, 1,3,5-trimethylbenzene, benzoic acid nitrile, perchloro biphenyl, 1,3-butadiene, 2-methyl-1,3-butadiene, butane, butanoic acid nitrile, carbon disulfide, carbon tetrachloride, chloroform, cyclohexane, methyl cyclohexane, perfluoro cyclohexane, cyclopentane, decalin, decane, ethane, bromoethane, chloroethane, 1,2-dibromoethane, 1,1-dichloroethane, difluoro-tetrachloro ethane, nitroethane, pentachloroethane, 1,1,2,2-tetrachloroethane, 1,1,2-trichloro ethane, trichloro-trifluoro ethane, ethylene, perchloroethylene, trichloroethene, heptane, perfluoroheptane, hexane, hexene-1, malonic acid dinitrile, methane, bromomethane, dichloromethane, dichloro-difluoro methane, dichloromethane, nitromethane, tetrachloro-difluoro methane, trichloro-monofluoro methane, naphthalene, nonane, octane, pentane, 1-bromopentane, 1-chloropentane, pentene-1, phenanthrene, propane, 1-bromopropane, 2,2-dimethylpropane, 1-nitropropane, 2-nitropropane, propene, 2-methylpropane, propionic acid nitrile, styrene, hydrogenated terphenyl, tetralin toluene and m-xylene.

Examples of liquid moderately polar diluents from which the appropriate diluent can be selected are: acetic acid butyl ester, acetic acid ethyl ester, acetic acid methyl ester, acetic acid pentyl ester, acetic acid propyl ester, N,N-diethyl acetic acid amide, N,N-dimethyl acetic acid amide, acrylic acid butyl ester, acrylic acid ethyl ester, acrylic acid methyl ester, adipic acid dioctyl ester, benzoic acid ethyl ester, benzoic acid methyl ester, 1-iodobutane, carbonic acid ester, vinyl chloride, N,N-diethyl formic acid amide, N,N-dimethyl formic acid amide, formic acid ethyl ester, formic acid methyl ester, formic acid 2-methylbutyl ester, formic acid propyl ester, furan, furfural, lactic acid butyl ester, lactic acid ethyl ester, methacrylic acid butyl ester, methacrylic acid ethyl ester, methacrylic acid methyl ester, oxalic acid diethyl ester, oxalic acid dimethyl ester, 1-iodopentane, phosphoric acid triphenyl ester, phosphoric acid tri-2-toly ester, phthalic acid dibutyl ester, phthalic acid diethyl ester, phthalic acid dihexyl ester, phthalic acid dimethyl ester, phthalic acid di-2-methylnonyl ester, phthalic acid dioctyl ester, phthalic acid dipentyl ester, phthalic acid dipropyl ester, propionic acid ethyl ester, propionic acid ethyl ester, propionic acid methyl ester, 1-methyl 2-pyrolidone, sebacic acid dibutyl ester, sebacic acid dioctyl ester and stearic acid butyl ester.

Examples of liquid hydrogen-bonded diluents from which the appropriate diluent can be selected are: N-ethyl formic acid amide, N-methyl formic acid amide and N-methyl methacrylic acid amide.

Mixtures of inert diluents can be used.

The heterogeneous catalytic reactions of the invention can be effected, for example, in one of three ways: (1) in batch processes; (2) in continuous fixed-bed processes; and (3) in continuous fluidized reactor processes. In a batch reactor, the catalyst is kept suspended in the reactant by shaking or stirring. In a fluidized reactor, the catalyst is at a particular original level. As the velocity of the reactant stream is increased, the catalyst bed expands upward to a second level, and at a critical velocity it enters into violent turbulence. The fluidized reactor is particularly useful for removing or supplying the heat necessary to maintain a fixed catalyst temperature. The fluidized reactor can usually be employed only on a rather large scale since good fluidization requires a reactor larger than about 1.5 inch in diameter.

The process of the invention broadly involves the liquid or gaseous use of anion-bound metal oxide heterogeneous catalysts for the alkoxylation of active-hydrogen compounds, preferably hydroxyl-containing compounds, such as, primary or secondary alcohols, diols or triols. Mixtures of active-hydrogen compounds can be used.

Active-hydrogen organic and inorganic compounds include, for example, hydrogen-containing compounds (ROH, polyols), carboxylic acids ($RCO_2H$), thiols (RSH), amines ($RNH_2$ or $R_2NH$), ammonia, water, hydrohalic acids (HX where X is a halogen), alkyl-$OCH_2CH_2OH$, HCN, and bisulfites of metals such as alkali and alkaline earth metals. R above is generally a saturated aliphatic hydrocarbon moiety (branched or unbranched alkanes), a saturated monocyclic moiety or an aromatic hydrocarbon moiety (i.e., an arene moiety). Such organic moieties can be substituted with nonreactive or non-interfering substituents such as halogens, $NO_2$, etc. The active-hydrogen compounds broadly have the formula HQ (where Q is a saturated or aromatic organic moiety or an inorganic moiety).

The invention can be used to alkoxylate any of the primary or secondary monohydric alcohols, dihydric alcohols (diols), trihydric alcohols and polyhydric alcohols (polyols), glycol ethers and alkoxylated ethylene glycols, all of which are suitable active-hydrogen compounds provided any particular individual compound does not poison the anion-bound metal oxide catalyst. Such hydroxyl-containing compounds can be substituted with non-interfering groups, such as, nitro groups, halo groups and the like.

The monohydric alcohols can be the primary alkyl (monohydric) alcohols having 1 to 12 carbon atoms, such as, methanol, ethanol, n-propanol, n-butanol, 1-pentanol, 1-hexanol, 1-heptanol, 1-octanol, 1-decanol, 1-dodecanol, isopropanol, isobutanol, 2-methyl-1-butanol, 3-methyl-1-butanol, 2-methyl-1-pentanol, 3-methyl-1-pentanol, 4-methyl-1-pentanol, 2-ethyl-1-butanol, and 2,4-dimethyl-1-pentanol. The monohydric alcohols can be the secondary alkyl (monohydric) alcohols having 2 to 12 carbon atoms, such as, 2-butanol, 2-pentanol, 3-methyl-2-butanol, 2-hexanol, 3-hexanol, 3-methyl-2-pentanol, 4-methyl-2-pentanol, 2,4-methyl-3-pentanol, and 2-octanol. The monohydric alcohols can be paraffinic alcohols (the above alkyl-alcohols) or olefinic alcohols (e.g., allyl alcohol). The monohydric alcohols can be alicyclic monohydric alcohols having 3 to 10 carbon atoms, such as, cyclohexanol, cycloheptanol, cyclopropanol, cyclobutanol, cyclopentanol and cyclooctanol.

The invention process can be used to alkyoxylate any of the aliphatic, aromatic or heterocyclic compounds containing two hydroxy groups, preferably separated by at least two carbon atoms. The diols can be substituted if desired with various noninterfering (non-functional) substituents such as ether groups, sulphone groups, tertiary amine groups, thioether groups, chlorine atoms, bromine atoms, iodine atoms, fluorine atoms, etc. Typical compounds which can be used are listed below merely by way of illustration and not limitation: Ethylene glycol, diethylene glycol, 2,2-dimethyl propane-1,3-diol, butane-1,4-diol, hexane-1,6-diol, octane-1,8-diol, decane-1,10-diol, dodecane-1,12-diol, butane-1,2-diol, hexane-1,2-diol, 1-O-methyl glycerol, 2-O-methyl glycerol, cyclohexane-1,4-methyl-diol, hydroquinone, resorcinol, catechol, bis(parahydroxyphenyl) butane, 4,4'-dihydroxybenzophenone, napthalene-1,5-diol, biphenyl-4-4'-diol, 2,2-bis(3-methyl-4-hydroxyphenyl) propane, 2,2-bis(4-hydroxy-dibromophenyl) propane, etc.

Mixtures of different diols can be used. It is also within the purview of the invention, though less preferred, to use the compounds containing more than two hydroxy groups, for example, glycerol, diglycerol, hexanetriol, pentaerythritol, etc. Moreover, it is within the scope of the invention to utilize the sulfur analogues of the diols. Thus, for example, instead of using the compounds containing two hydroxy groups, one can use the analogues containing either (a) two —SH groups or (b) one —SH group and one —OH group.

Among the preferred compounds are the aliphatic diols, for example, those of the type:

$$HO-(CH_2)_n-OH$$

wherein n has a value from 2 to 12. Another category of aliphatic hydroxyl-containing compounds are the polyethylene glycols, i.e.:

$$HO-CH_2-CH_2-[O-CH_2-CH_2]_n-O-CH_2-CH_2-OH$$

wherein n has a value from zero to 10. A category of aromatic diols are the bisphenols, that is, compounds of the type:

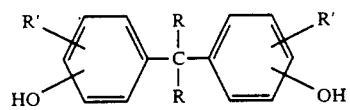

wherein R—C—R represents an aliphatic hydrocarbon group containing 1 to 12 carbon atoms and R' represents hydrogen or a lower alkyl radical. In this category are: 2,2-bis(parahydroxyphenyl) propane; 2,2-bis(3-isopropyl-4-hydroxyphenyl) propane; and brominated derivatives of bisphenol A, such as, 2,2-bis(4-hydroxydibromophenyl) propane.

The alkoxylation of diols can provide dimers or polymers.

The useful trihydric alcohols include glycerol, 1,2,3-butantriol and 1,1,1-trihydroxymethylethane. The useful polyhydric alcohols include those having the formula $CH_2OH(CHOH)_nCH_2OH$, wherein n is 2 to 5, such as, arabitol, adonitol, xylitol, mannitol and sorbitol.

Preferably the invention alkoxylation process is used with glycol ethers, ethylene glycols (i.e., to produce CARBOWAX®-type products) or Tergitol-type products.

CARBOWAX® is the registered trademark of Union Carbide Corporation for a series of polyethylene glycols. Ethylene glycol can be used to make the CARBOWAX® polyethylene glycols or the CARBOWAX® polyethylene glycols can be used to make higher molecular weight CARBOWAX® polyethylene glcyols. For example, CARBOWAX® polyethylene glycol 200 can be used to make CARBOWAX® polyethylene glycol 400. Specifically, the CARBOWAX® polyethylene glycols are liquid and solid polymers of the general formula $H(OCH_2CH_2)_nOH$, where n is greater than or equal to 4. In general, each CARBOWAX® polyethylene glycol is followed by a number which corresponds to its average molecular weight. Generally, the invention process is not preferred for using CARBOWAX® polyethylene glycols having an average molecular weight above about 600 to 800 as starting materials because such CARBOWAX® polyethylene glycols are solids at room temperature (although they are liquid at the reaction temperatures, e.g., 110° C.). Examples of useful CARBOWAX® polyethylene glycols are: CARBOWAX® polyethylene glycol 200, which has an average n value of 4 and a molecular weight range of 190 to 210; CARBOWAX® polyethylene glycol 400, which has an average n value between 8.2 and 9.1 and a molecular weight range of 380 to 420; and CARBOWAX® polyethylene glycol 600, which has an average n value between 12.5 and 13.9 and a molecular weight range of 570 to 630.

The anion-bound zirconium oxide catalyst has a high selectivity to ethylene glycol. The reaction temperature is not important and can be run at 50° to 110° C. at a 5:1 weight ratio of $H_2O$ to ethylene oxide and at various catalyst concentrations greater than 90 percent of ethylene glycol is produced. At a 10:1 weight ratio, greater than 95 percent of ethylene glycol is produced.

TERGITOL® is the registered trademark of Union Carbide Corporation for a series of the sodium salts of the acid sulfate of secondary alcohols of 10 to 20 carbon atoms which are nonionic or anionic surfactants. Examples of the TERGITOL® are: TERGITOL® Pentrant 08, which is $C_4H_9CH(C_2H_5)CH_2SO_4$—Na; TERGITOL® Pentrant 4, which is $C_4H_9CH(C_2H_5)C_2H_4CH$—$(SO_4Na)CH_2CH(CH_3)_2$; and TERGITOL® Pentrant 7, which is $C_4H_9CH(C_2H_5)C_2H_4CH$—$(SO_4Na)C_2H_4CH(C_2H_5)_2$.

Examples of useful glycol ethers are ethylene glycol monoethyl ether, ethylene glycol monobenzyl ether, ethylene glycol monobutyl ether, ethylene glycol monomethyl ether, ethylene glycol monohexyl ether, ethylene glycol monophenyl ether, ethylene glycol monooctyl ether, propylene glycol monomethyl ether and propylene glycol phenyl ether.

The active-hydrogen compound can be a saturated carboxylic acid, HOCOR. The carboxylic acid can be a straight-chain alkanoic acid ($C_nH_{2n}O$, wherein n is 1 to 35), such as, methanoic acid, ethanoic acid, propanoic acid, butanoic acid, pentanoic acid, hexanoic acid, heptanoic acid, octanoic acid, nonanoic acid, decanoic acid, undecanoic acid, dodecanoic acid, tridecanoic acid, tetradecanoic acid, pentadecanoic acid, hexadecanoic acid, heptadecanoic acid, octadecanoic acid, nonadecanoic acid, eicosanoic acid, docosanoic acid, tetracosanoic acid, hexacosanoic acid, octacosanoic acid, triacontanoic acid, tritriacontanoic acid, and pentatriacontanoic acid. The active-hydrogen compound can be a branched alkanoic acid, such as, isopropanoic acid, isobutanoic acid, 2-butanoic acid, 3-methyl-1-butanoic acid, 2-methyl-1-butanoic acid, 2-pentaonoic acid, 3-pentanoic acid, 2-methyl-1-pentanoic acid, 3-methyl-1-pentanoic acid, 2-ethyl-1-butanoic acid, 2-hexanoic acid, 3-hexanoic acid, 2-methyl-2-pentanoic acid, 2,4-dimethyl-3-pentanoic acid and 2-octanoic acid.

The carboxylic acid can be a dienoic acid ($C_nH_{2n-4}O_2$), such as, 2,4-pentadienoic acid, 2,4-hexadienoic acid, 2,4-decadienoic acid, 2,4-dodecadienoic acid cis-9-, cis-12-octadecadienoic acid, trans-9, trans-12-octadecadienoic acid, and 9,13-docosadienoic acid. The carboxylic acid can also be a trienoic acid ($C_nH_{2n-6}O_2$), such as, 6,10,14-hexadecatrienoic acid, cis-9-, cis-12, cis-15-octadecatrienoic acid, cis-9-, trans-11, trans-13-octadecatrienoic acid trans-9, trans-11, trans-13-octadecatrienoic acid cis-9-, cis-11, trans-13-octadecatrienoic acid, and trans-9, trans-12, trans-15-octadecatrienoic acid. The carboxylic acid can further be a tetraneoic acid ($C_nH_{2n-8}O_2$), such as, 4,8,12,15-octadecatetraenoic acid, 9,11,13,15-octadecatetraenoic acid, 9,11,13,15-octadecatetraenoic acid, and 5,8,11,14-eicosatetraenoic acid. The carboxylic acid can also be a pentaenoic acid ($C_nH_{2n-10}O_2$), such as, 4,8,12,15,19-docosapentaenoic acid.

The carboxylic acid can be a substituted, saturated carboxylic acid, such as, iodoacetic acid, o-nitrophenylacetic acid, p-nitrophenylacetic acid, trichloroacetic acid, trifluoroacetic acid, bromoacetic acid, 2-bromobutyric acid, 2-bromohexadecanoic acid, 2-bromohexanoic acid, 6-bromohexanoic acid, 2-bromo-3-methylbutyric acid, (p-bromophenoxy)acetic acid, 2-bromopropionic acid, 3-bromopropionic acid, 11-bromoundecanoic acid, chloroacetic acid, 3-chlorobutyric acid, 3-chloro-2,2-dimethylpropionic acid, (4-chloro-2-methylphenoxy)acetic acid, o-chlorophenoxyacetic acid, p-chlorophenoxyacetic acid, 2-(o-chlorophenoxy)propionic acid, p-chlorophenylacetic acid, 2-chloropropionic acid, 3-chloropropionic acid, 2,3-dibromopropionic acid, dichloroacetic acid, 2,4-dichlorophenoxyacetic acid, (2,5-dihydroxyphenyl)acetic acid, (3,4-dimethoxyphenyl)acetic acid, 2,4-dinitrophenylacetic acid, (2,4-di-tert.-pentylphenoxy)acetic acid, 2-(2,4-di-tert.-pentylphenoxy)butyric acid, ethoxyacetic acid, 3,11-dihydroxytetradecanoic acid, 2,15,16-trihydroxyhexadecanoic acid, aleoprolic acid and aleprestic acid. Normally, the substituents on any of the active-hydrogen compounds should be non-interfering, but if desired, substituents having active hydrogens, such as, —OH or —SH, can be used (of course, not all —OH and —SH substituents will be reactive).

The active-hydrogen compounds can be a sulfonic acid, $RSO_3H$, wherein R is a univalent organic radical (saturated, alicyclic or aromatic), such as, the alkanesulfonic acids, for example, methanesulfonic acid, ethanesulfonic acid, propanesulfonic acid, butanesulfonic acid, pentanesulfonic acid and hexanesulfonic acid, alkarenesulfonic acids ($R_nARSO_3H$, where R is alkyl and n is 1 to 3), such as, p-toluenesulfonic acid, arenesulfonic acids, such as, 2-naphthalenesulfonic acid, 1,3-benzenedisulfonic acid, 2,6-naphthalenedisulfonic acid and 1,3,6,8-naphthalenetetrasulfonic acid, fluorinated and chlorofluorinated sulfonic acids, such as, $CF_3SO_3H$, $ClCF_2SO_3H$, $Cl_2CFSO_3H$, $CHF_2SO_3H$ and $ClCHFSO_3H$, other substituted sulfonic acids, such as, p-hydroxybenzene sulfonic acid, and other sulfonic acids, such as, methanedisulfonic acid and methanetrisulfonic acid.

The active-hydrogen compounds can be other sulfur acids where sulfur is substituted for one or more oxygens in the carboxylic group, such as, methanethiolic acid (HCOSH), methanethionic acid (HCSOH), ethanethionic acid (CH₃COSH), ethanethionic acid (CH₃CSOH), methanethionothiolic acid (HCSSH) and ethanethionothiolic acid (CH₃CSSH).

The active-hydrogen compounds can be alkanethiols (e.g., having 1 to 20 carbon atoms), such as, methanethiol, ethanethiol, 2-propanethiol, 1-propanethiol, 2-methyl-2-propanethiol, 2-butanethiol, 2-methyl-1-propanethiol, 1-butanethiol, 1-pentanethiol, 1-hexanethiol, 1-heptanethiol, 1-octanethiol, 1-decanethiol, 1-dodecanethiol, 1-hexadecanethiol, 1-octadecanethiol, and cyclohexanethiol, and aromatic thiols, such as, benzene thiol (or phene thiol). Besides monothiols, other thiols can be used such as dithiols, trithiols and tetrathiols (e.g., 1,2-ethanedithiol), and substituted thiols (e.g., 1-amino-2-propane thiol).

Thioglycolic acid and other sulfur analogue acids can be used as the active-hydrogen compound.

The active-hydrogen compounds can be alkyl-OCH₂CH₂OH, such as, Cellosolve TM (C₂H₅OCH₂CH₂OH), methyl Cellosolve TM and butyl Cellosolve TM.

The active-hydrogen compounds can be bisulfites of metals, such as, NaHSO₃, KHSO₃, LiHSO₃, Mg(HSO₃)₂, Zn(HSO₃)₂ and Be(HSO₃)₂.

The alkoxylating compounds used in the invention alkoxylation process are epoxide compounds having the formula:

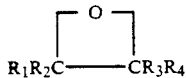

wherein $R_1$, $R_2$, $R_3$ and $R_4$ are each H or $-(CH_2)_n CH_3$, and wherein n is 0 to 3, with the proviso that $R_1$, $R_2$, $R_3$ and $R_4$ can be the same or different. The useful epoxides are basically derivatives of ethylene oxide. Examples of the alkoxylating compound are ethylene oxide, propylene oxide, trimethylene oxide (2-methyloxirane), isobutylene oxide, 2,2,3-trimethyloxirane, cis-2-butene oxide, trans-2-butene oxide, α-butylene oxide, 2,2,3,3,-tetramethyloxirane, 2,3-diethyleneoxirane, 2,3-dipropyleneoxirane, 2,3-dibutyleneoxirane, 2-butyleneoxirane, 2-isobutyleneoxirane and 2-ethylene-3-propylene oxirane. The preferred alkoxylating agent is ethylene oxide because it is much more reactive than propylene oxide and the higher members of the subject epoxide compounds.

A narrow molecular weight range of products is produced with a minimum of undesirable high molecular weight by-products or co-products.

The following examples are illustrative of the invention.

EXAMPLE 1

Preparation Of Sulfate-Bound Zirconium Oxide Catalyst 500 ml. of NH₄OH (14.8M), 500 ml. of distilled water and 64.5 g of zirconyl chloride (yellow solid) were combined and the mixture was placed in a 2 liter beaker having a watchglass cover. The solution was stirred for 3 hours. A fine white solid formed quickly as the stirring began. The liquid was filtered off in a Buchner funnel. The solid filtrate was placed in a vacuum oven and dried at 100° C. and 30 inches of vacuum. After drying in the vacuum oven, about 35 g of white solid was obtained. The solid was washed in a Buchner funnel using a total of 25 ml. of water. The solid was then treated with 1N H₂SO₄ in the form of an acidic aqueous solution (pH 1). The solid was divided and placed in two Pyrex tubes. The solid was calcined for 3 hours at 600° C. (with air flow). The calcined solid was light yellow and was sulfate-bound zirconium oxide (catalyst). 29.6 g of the catalyst was obtained. The pH of the catalyst in water was acidic.

EXAMPLE 2

Preparation Of CARBOWAX ® Polyethylene Glycol 200 Using Sulfate-Bound Zirconium Oxide Catalyst 50.7 g of ethylene glycol and 5.0 g of sulfate-bound zirconium oxide catalyst (prepared by the method of Example 1) were charged to a Parr bomb. The bomb, three times, was purged with N₂ and evacuated. The bomb was left under 15 pounds per square inch gauge of pressure of N₂. The bomb was heated and stirred vigorously. Ethylene oxide was added to the bomb based on the following schedule:

TABLE I

| Time, Mins. | Reactor Temp., °C. | Reactor Pressure, p.s.i.g. 1 | Total Ethylene Oxide Feed, grams |
|---|---|---|---|
| 0 | 84° | 18/41 | 6.0 |
| 4 | 96° | 24/36 | 8.1 |
| 7 | 86° | 24/40 | 13.2 |
| 10 | 81° | 24/36 | 16.1 |
| 14 | 79° | 24/36 | 19.8 |
| 17 | 81° | 24/40 | 25.7 |
| 23 | 78° | 24/42 | 32.1 |
| 31 | 82° | 24/39 | 37.1 |
| 40 | 79° | 24/37 | 40.6 |
| 48 | 81° | 26/43 | 46.2 |
| 59 | 84° | 27/45 | 52.2 |
| 73 | 82° | 29/44 | 57.6 |
| 90 | 81° | 30/41 | 61.1 |
| 163 | 84° | 29/45 | 67.2 |
| 212 | 84° | 30/45 | 71.9 |
| 234 | 104° | 33/54 | 75.3 |
| 241 | 93° | 34/56 | 80.2 |
| 261 | 99° | 36/51 | 90.0 |
| 307 | 97° | 38/60 | 94.2 |
| 322 | 98° | 41/63 | 99.6 |
| 349 | 97° | 42/65 | 105.1 |
| 355 | 96° | 57/65 | 106.9 |
| 370 | 97° | 52/68 | 110.8 |
| 375 | 97° | 62/67 | 112.8 |
| 400 | 98° | 54 | 112.8 |
| 600 | 16° | 35 | |

Note:
1. The first number is the pressure before the ethylene oxide addition, and the second number is the pressure after the ethylene oxide addition.

An exotherm of 8° to 9° C. occurred immediately after the ethylene oxide was added to the bomb. The pressure began to quickly drop. Further exotherms of 8° to 9° C. occurred after each addition of ethylene oxide through the addition totalling 40.6 grams. Then no exotherm was observed in conjunction with ethylene oxide additions until the addition totalling 67.2 grams. At that an exotherm of 4° to 5° C. occurred. Even larger exotherms occurred thereafter at some of the subsequent ethylene oxide additions. The temperature was raised to 100° C. before the addition totalling 75.3 grams. The pressure dropped back quickly and completely after ethylene oxide additions during the first part of the run, but slowed somewhat later in the run. (The pressure dropped faster after reaching 28 p.s.i.g.) Pressure also began building later in the run, but this was partly a function of the increased temperature. (The pressure rose from 31 p.s.i.g. to 33 p.s.i.g. when the temperature was raised to 100° C.) After 600 minutes the heat was shut off from the bomb. The product was slightly hazy (possibly due to fine catalyst particles in suspension therein), had a pH of 7 and was slightly viscous. The product was analyzed using vapor phase chromatography. The product was CARBOWAX® polyethylene glycol 200 produced by the ethoxylation of ethylene glycol.

The sulfate-bound zirconium oxide catalyst was recovered using a fine sintered glass funnel. The recovered catalyst was washed with ethylene glycol—the pH at this point of the catalyst in water was neutral. The catalyst was then washed with methyl alcohol—the pH was neutral. The catalyst was dried in an oven at 130° C.; after 1.5 hours the pH of the catalyst was 3; and after 3 hours the pH of the catalyst was 3. The recovered catalyst was then calcined for 1.5 hours at 575° C. with an airflow.

EXAMPLE 3

Preparation of Methyl Cellosolve TM Using Sulfate-Bound Zirconium Oxide Catalyst 50.0 g (1.56 moles) of methanol, containing 0.225 percent of water, and 1.0 g of sulfate-bound zirconium oxide catalyst (prepared by the method of Example 1) were charged to a Parr bomb. The bomb was purged with $N_2$ and evacuated three times. The bomb was left under 16 p.s.i.g. of $N_2$. The bomb was heated and stirred vigorously. Ethylene oxide was added to the bomb based on the following schedule:

TABLE II

| Time, Mins. | Reactor Temp., °C. | Reactor Pressure, p.s.i.g. | Total Ethylene Oxide Feed, grams |
| --- | --- | --- | --- |
| 0 | 81° | 34/38 | 3.5 |
| 19 | 79° | 35/35 | 7.1 |
| 70 | 79° | 36/46 | 12.0 |
| 123 | 79° | 40/47 | 17.2 |
| 179 | 79° | 44 | |
| overnite | 16° | 20 | |

It took 7 minutes for the pressure to reach 36 p.s.i.g. in the bomb, at which time the first addition was made. The pressure reached 36 p.s.i.g. at the 45 minute point. The reactants reacted at the moderate rate, i.e., "cooked down" well. After 179 minutes the heat was shut off from the bomb. The product was methyl Cellosolve TM produced by the ethoxylation of methanol.

EXAMPLE 4

Example 3 was repeated, except that the starting methanol contained 0.768 percent of water (water was added). The reaction occurred at about the same rate as in Example 3, but the reaction "cooked down" to slightly lower pressure. The product was methyl Cellosolve TM produced by the ethoxylation of methanol.

EXAMPLE 5

Example 3 was repeated, except that the starting methanol contained 0.0315 percent water. The methanol was dried over activated 4 A sieves. The reaction occurred at about the same rate as and "cooked down" similarly to Example 3. The product was methyl Cellosolve TM produced by the ethoxylation of methanol.

All of the above water determinations in Examples 3 to 5 were made on a Photovolt Aquatest IV electronic titrator.

The purpose of Examples 3 to 5 was to determine the effect of water content on the preparation of methyl Cellosolve TM using sulfate-bound zirconium oxide catalyst. The reactions in Examples 3 to 5 were run with all of the conditions the same except for the water content of the starting alcohol. Water did not seem to adversely effect the reaction rate, in fact, a slight increase in activity was observed. The conversion to product could not be correlated with the water content. A peak was observed in all of the vapor phase chromatography scans with retention time similar to ethylene glycol, but the area percent of this peak did not vary significantly between runs.

EXAMPLE 6

Preparation Of CARBOWAX® Polyethylene Glycol Using Sulfate-Bound Zirconium Oxide Catalyst 52.9 g of ethylene glycol and 5.0 g of sulfate-bound zirconium oxide catalyst was charged to a Parr bomb. The bomb was purged with $N_2$ and evacuated three times. The bomb was left under 16 p.s.i.g. of $N_2$. The bomb was heated to 80° C. and stirred vigorously. Ethylene oxide was added to the bomb based on the following schedule:

TABLE III

| Time, Mins. | Reactor Temp., °C. | Reactor Pressure, p.s.i.g. | Total Ethylene Oxide Feed, grams |
| --- | --- | --- | --- |
| 0 | 78° | 19/40 | 6.4 |
| 6 | 77° | 20/40 | 12.4 |
| 12 | 77° | 22/44 | 19.4 |
| 21 | 82° | 23/44 | 26.4 |
| 30 | 77° | 24/43 | 33.4 |
| 45 | 81° | 26/46 | 41.1 |
| 48 | 80° | 28 | |

An exotherm of about 30° C. occurred upon the first addition of ethylene oxide. The ethylene oxide was rapidly consumed. The exotherms became smaller on subsequent additions. At the six minute addition, the exotherm went to 99° C. At the 30 minute addition, the exotherm went to 84° C. At the 45 minute addition, the exotherm went to 85° C. The rate of ethylene oxide consumption also decreased, and the pressure built up somewhat in the bomb (possibly due to volume effect). After 48 minutes the heat was turned off and the catalyst was filtered off from the liquid product. The product was analyzed using vapor phase chromatography. The sample tested contained 0.21 percent of dioxane. The product was clear and colorless and had a neutral pH. The product was CARBOWAX® polyethylene glycol (viscous liquid polyethylene glycol) prepared by the ethoxylation of ethylene glycol.

EXAMPLE 7

Preparation of CARBOWAX® Polyethylene Glycol Using Sulfate-Bound Zirconium Oxide Catalyst The filtered sulfate-bound zirconium oxide catalyst (5.0 g) from Example 6 was placed in a Parr bomb. The catalyst was not washed, so a small amount of the liquid product of Example 6 remained in the bomb. 50.7 g of ethylene glycol was charged to the bomb. The bomb was purged with $N_2$ and evacuated three times. The bomb was left under 16 p.s.i.g. of $N_2$. The bomb was heated and stirred vigorously. Ethylene oxide was added to the bomb based on the following schedule:

TABLE IV

| Time, mins. | Reactor Temp., °C. | Reactor Pressure, p.s.i.g. | Total Ethylene Oxide Feed, grams |
| --- | --- | --- | --- |
| 0 | 81° | 19/37 | 6.2 |
| 9 | 79° | 22/42 | 11.9 |
| 17 | 77° | 24/39 | 16.5 |
| 27 | | 24 | |

An exotherm to 90° C. occurred upon the first addition of ethylene oxide. The exotherm was not as great as and the rate of reaction was slower than the initial reaction in Example 6. At the 9 minute addition, the exotherm went to 88° C. At the 17 minute addition, the exotherm went to 86° C. The catalyst apparently lost some activity during the reaction. After 27 minutes the heat was turned off and the bomb was allowed to set at room temperature for about 64 hours. The product was analyzed using vapor phase chromatography. The sample tested contained 0.29 percent of dioxane. The product was clear and colorless, and had a neutral pH. The product was CARBOWAX ® polyethylene glycol prepared by the ethoxylation of ethylene glycol.

EXAMPLE 8

Preparation of CARBOWAX ® Polyethylene Glycol Using Sulfate-Bound Zirconium Oxide Catalyst 42.3 g of ethylene glycol and 4.2 g of sulfate-bound zirconium oxide catalyst were charged to a Parr bomb. The bomb was purged with $N_2$ and evacuated three times. The bomb was left under 16 p.s.i.g. of $N_2$. The bomb was heated and stirred vigorously. Ethylene oxide was charged to the bomb based on the following schedule:

TABLE V

| Time, mins. | Reactor Temp., °C. | Reactor Pressure, p.s.i.g. | Total Ethylene Oxide Feed, grams |
| --- | --- | --- | --- |
| 0 | 82° | 18/41 | 6.4 |
| 9 | 77° | 20/41 | 12.3 |
| 21 | 80° | 22/46 | 18.8 |
| 61 | 81° | 22 | |

An exotherm went to 99° C. upon the first addition of the ethylene oxide. The ethylene oxide was consumed fairly rapidly. The second addition of ethylene oxide produced only a small exotherm (to 84° C.) and the reaction slowed considerably. At the 21 minute addition, the exotherm went to 82° C. The product was analyzed using vapor phase chromatography, indicating that a substantial amount of product was produced. The sample contained 0.12 percent of dioxane. The product was colorless and slightly hazy (probably due to catalyst in suspension). The product was CARBOWAX ® polyethylene glycol prepared by the ethoxylation of ethylene glycol.

EXAMPLE 9

Hydrolysis Of Zirconyl Chloride 500 ml. of distilled water and 64.5 g of $ZrOCl_2.8H_2O$ were placed in a beaker and mixed. 40 ml. of concentrated $NH_4OH$ solution was added with mixing to the beaker. The pH of the mixture was about 10. 8.4 ml. of concentrated HCl solution was added to the admixture to bring the pH back to 7. The admixture was filtered on a M sintered glass funnel. The pH of the solid filtrate in water was neutral. The solid filtrate was placed in a large Soxhlet extractor mounted on a 2 liter flask. The solid filtrate was washed with distilled water in the Soxhlet extractor. The liquid mixture was refluxed in the Soxhlet extractor for 13.5 hours. A check of the solid for Cl was essentially negative. The solid was dried overnight in a vacuum oven at 100° to 110° C. and 30 inches of vacuum over $MgSO_4$. The solid was slightly off white and had the consistency of talcum powder (very fine). The solid was not a hard cake as had been previously observed in this example. 28.09 g of the solid were recovered—the solid had a neutral pH in water. The solid was placed in 400 ml. of distilled water. Stirring was started and the pH was 7. After stirring for 2 hours the pH was still neutral. The liquid admixture was filtered on a C sintered glass funnel. Some of the solid passed through the filter. The solid filtrate was placed in a vacuum oven at 80° C. and at 30 inches of vacuum over $MgSO_4$. The filtrate was dried over a weekend in the vacuum oven (the temperature reached 90° C.). The solid was slightly off-white in color and was a fine free-flowing powder. The pH of the solid in water was neutral; this was the first time the pH indicated neutral for $Zr(OH)_4$. The product was zirconium hydroxide.

EXAMPLE 10

Preparation of Various Anion-Bound Zirconium Oxide Catalysts

Four samples of $Zr(OH)_4$ (prepared by the method of Example 10) were each treated with a different solution, respectively, of $NH_4BF_4$, $(NH_4)_2HPO_4$, $(Me_4N)PF_6$ and $H_2SO_4$. $(Me_4N)PF_6$ is tetramethylammoniumhexafluorophosphate. $NH_4BF_4$ is ammonium tetrafluroborate. Reference is made to Table VI below for the treating agents and other pressing data. Each $Zr(OH)_4$ sample in the respective solution was stirred for 5 to 10 minutes and then filtered on a Buchner funnel. Each of the four solids was calcined in a Pyrex tube at 575° C. (with an air flow) for 3 hours.

TABLE VI

| $Zr(OH)_4$ Sample | Treated with[1] | In Solution | pH of Solution | g.$Zr(OH)_4$/ ml. Soln. | pH in $H_2O$ after calcining | Notes |
| --- | --- | --- | --- | --- | --- | --- |
| First | $NH_4BF_4$ | 10.48 g/100 ml $H_2O$ | 4 | 5 g/78 ml | 3 to 4 | off-white after calcining |
| Second | $(NH_4)_2HPO_4$ | 1N$(NH_4)_2HPO_4$ | 9 | 5 g/78 ml | 2 to 3 | off-white after calcining |
| Third | $(Me_4N)PF_6$ | 21.9 g/100 ml $H_2O$ insoluluble, added more $H_2O$, still insoluble | 7 | 5 g/78 ml | 4 | black color after calcining- probably carbon |
| Fourth | $H_2SO_4$ | 1N $H_2SO_4$ | | 11.3 g/170 ml | 1 to 2 | yellow after calcining; white after |

TABLE VI-continued

| Zr(OH)₄ Sample | Treated with[1] | In Solution | pH of Solution | g.Zr(OH)₄/ ml. Soln. | pH in H₂O after calcining | Notes |
|---|---|---|---|---|---|---|
| | | | | | | cooled |

Note: 1. me is methyl 5 g of the calcined filtrate from the sulfuric acid treated material was washed overnight with distilled water in a Soxhlet extractor. The distilled water after the wash had a pH of 2 to 3 and had a very fine, white, gelatinous solid floating in it. The wash water tested positive for SO₄(BaCl₂ test). The solid was removed from the Soxhlet extractor. The solid in water had a pH of 4. The solid was then calcined in a Pyrex tube at 575° C. (with an air flow) for 3.5 hours. After calcining the solid was yellow; upon cooling, the solid turned light yellow. The solid product in water had a pH of 2. The product was sulfate-bound zirconium oxide catalyst.

EXAMPLE 11

Preparation Of CARBOWAX ® Polyethylene Glycol Using Phosphate-Bound Zirconium Oxide Catalyst 42.9 g of ethylene glycol and 4.17 g of zirconium oxy acid phosphate catalyst (as prepared in Example 10) were charged to a Parr bomb. The bomb was purged with N₂ and evacuated three times. The bomb was left under 16 p.s.i.g. of N₂. The bomb was heated and stirred vigorously. Ethylene oxide was charged to the bomb based on the following schedule:

TABLE VII

| Time, mins. | Reactor Temp., °C. | Reactor Pressure, p.s.i.g. | Total Ethylene Oxide Feed, grams | Net Feed, grams[1] | Exotherm Top Temp., °C. | Net Temp. Increase, °C. |
|---|---|---|---|---|---|---|
| 0 | 82° | 19/43 | 5.9 | | 112° | 30° |
| 3 | 90° | 24/45 | 10.9 | | 112° | 22° |
| 7 | 83° | 24/45 | 16.5 | | 102° | 19° |
| 12 | 77° | 24/42 | 21.7 | | 90° | 13° |
| 17 | 77° | 24/39 | 27.3 | | 88° | 12° |
| 23 | 78° | 24 | — | | | |
| Reactor Restarted | | | | | | |
| 23 | 84° | 23/43 | 34.2 | 6.9 | 102° | 18° |
| 28 | 80° | 26/42 | 40.7 | 13.4 | 87° | 7° |
| 37 | 79° | 26/45 | 47.2 | 19.9 | 92° | 13° |
| 47 | 82° | 27/46 | 53.9 | 26.6 | 91° | 9° |
| 53 | 79° | 28/46 | 60.5 | 33.2 | 85° | |
| 80 | 82° | 36/50 | 68.1 | 40.8 | 84° | |
| 105 | 81° | 31/52 | 75.8 | 48.5 | 83° | |

Note: [1]Net ethylene oxide feed, in grams, after the reactor was restarted

Upon first adding ethylene oxide, a 30° C. exotherm occurred. Thereafter, the exotherms decreased. Also, the rate of reaction, which was very rapid at first, slowed as the reaction proceeded. During the run, the reaction was stopped after 23 minutes and later started up again by continued heating and further ethylene oxide additions. The liquid product was analyzed using vapor phase chromatography. The product contained 0.25 percent of dioxane. The product was clear and pinkish and was a little hazy (probably due to catalyst in suspension). The pinkish color was due to a bad batch of ethylene oxide, which had a slight color and fine particulates in it. The pH of the product was neutral. The catalyst was filtered off from the liquid product. At that point the pH of the catalyst was 1 to 2. After washing the catalyst with methanol, the slightly wet catalyst (from methanol) had a pH of 3. The product was CARBOWAX ® polyethylene glycol prepared by the ethoxylation of ethylene glycol.

EXAMPLE 12

Ethoxylation Of 1-Butanol Using Sulfate-Bound Zirconium Oxide Catalyst 57.9 g of 1-butanol and 4.96 g of sulfate-bound zirconium oxide catalyst (as prepared in Example 10) were charged to a Parr bomb. The pH of the mixture was neutral. The bomb was purged with N₂ and evacuated three times. The bomb was left under 17 p.s.i.g. of N₂. The bomb was heated and stirred vigorously. Ethylene oxide was charged to the bomb based on the following schedule:

TABLE VIII

| Time, mins. | Reactor Temp., °C. | Reactor Pressure, p.s.i.g. | Total Ethylene Oxide Feed, grams | Net Feed grams[1] | Exotherm Top Temp., °C. | Net Temp. increase, °C. |
|---|---|---|---|---|---|---|
| 0 | 81° | 21/30 | 7.8 | | 103° | 22° |
| 6 | 74° | 22/53 | 13.5 | | 78° | 4° |
| 18 | 2 | 24 | | | | |
| 24 | 104° | 26 | | | | |
| 26 | 118° | 28/40 | 17.9 | | 131° | 13° |
| 33 | 113° | 30/43 | 22.8 | | 125° | 12° |
| 40 | 105° | 30/43 | 27.8 | | 113° | 8° |
| 48 | 100° | 30/44 | 32.9 | | 105° | 5° |
| 56 | 112° | 38/44 | 35.3 | | 114° | 2° |
| 73 | 108° | 33³ | | | | |
| 73 | 17° | 21⁴ | | | | |
| 144 | 110° | 33/40 | 38.6 | 3.5 | 115° | |

TABLE VIII-continued

| Time, mins. | Reactor Temp., °C. | Reactor Pressure, p.s.i.g. | Total Ethylene Oxide Feed, grams | Net Feed grams[1] | Exotherm Top Temp., °C. | Net Temp. increase, °C. |
|---|---|---|---|---|---|---|
| 150 | 108° | 34/40 | 40.8 | 5.5 | 111° | |
| 161 | 110° | 34 | | | | |

Notes:
[1] Net etylene oxide fee, in grams, after
[2] Temperature was increased to about 100° C.
[3] The heat was turned off and the sealed bomb stood overnight.
[4] The test was resumed.

Upon first adding ethylene oxide, a 22° C. exotherm occurred with rapid reaction of the ingredients. The second ethylene oxide produced a much smaller exotherm and the reaction rate was slower. The temperature was raised to about 100° C., whereupon the rate of reaction was faster and the exotherms increased for awhile. After 73 minutes, the heat was shut off and the sealed bomb was allowed to set overnight. Two more additions of ethylene oxide were made. The bomb was evacuated before the sample was taken in order to remove excess ethylene oxide. The product was analyzed using vapor phase chromatography and shown to be ethoxylates of 1-butanol. It was difficult to determine that dioxane was produced due to the close proximity of dioxane retention time to that of 1-butanol. The liquid product was fairly clear, and had a slight color due to catalyst in suspension and from the bad batch of ethylene oxide. The pH of the product was neutral.

EXAMPLE 13

Hydrolysis of Zirconyl Chloride and Treatment With Sulfuric Acid.

16 g of $ZrOCl_2 \cdot 8H_2O$ was dissolved in 200 ml. of distilled water in a 500 ml. Erlenmeyer flask. 21 g of silica gel and 50 ml. of water (to aid stirring) were added. Enough $NH_4OH$ was added while stirring to obtain a pH of 7. The mixture became very thick as a white gelatinous precipitate formed. The solution was stirred for about one hour. A solid was filtered out and dried overnight in a vacuum oven at 80° to 90° C. and under 30 inches of vacuum over $MgSO_4$. 29.33 g of silica gel and a fine white solid was recovered. The material had a pH in water of 3. The material was sieved on a U.S. Pat. No. 8 screen to eliminate the fines—22.10 g of greater than 8 mesh material remained. The silica gel appeared to be coated with white material. The silica gel fizzed and broke up when placed in water. 22.10 g of the silica gel was treated with 166 ml. of 1N $H_2SO_4$ and then calcined in Pyrex tubes at 575° C. (with air flow) for 3 hours. The material appeared physically unchanged and still had a "coated" appearance. The pH of the material in water was 2 to 3. 20.2 g of the product was obtained. The solid product was sulfate-bound zirconium oxide catalyst bound to silica gel carrier.

EXAMPLE 14

Hydrolysis Of Zirconyl Chloride And Treatment With Sulfuric Acid 16 g of $ZrOCl_2 \cdot 8H_2O$ was dissolved in 200 ml. of distilled water in a 500 ml. Erlenmeyer flask. 41 g of 4 A sieves and 100 ml. of water (to aid stirring) were added. Enough $NH_4OH$ was added while stirring to obtain a pH of 7. The mixture became very thick as a white gelatinous precipitate formed. The solution was stirred for about one hour. A solid was filtered out and dried overnight in a vacuum oven at 80° to 90° C. and under 30 inches of vacuum over $MgSO_4$. The material had a neutral pH in water. The material was sieved on a U.S. Pat. No. 20 screen to eliminate the fines—49.49 g of the greater than 20 mesh material remained. The sieves appeared to have absorbed $Zr(OH)_4$, a white powder—very little fines were present. The sieves appeared to have white powder on their surface, but the color was uneven. 10 g. of the sieve material was treated with 75 ml of 1N $H_2SO_4$. Some white color went into the $H_2SO_4$. The $H_2SO_4$-treated sieve material was calcined in Pyrex tubes at 575° C. (with air flow) for 3 hours. Some fine particles were present after calcining. The pH of the sieve material in water was 5 to 6. The solid product was sulfate-bound zirconium oxide catalyst bound to 4 A sieves.

EXAMPLE 15

Preparation Of CARBOWAX ® Polyethylene Glycol Using Silica Gel-Supported Sulfate-Bound Zirconium Oxide Catalyst 155.2 g of ethylene glycol (a syrupy liquid) and 20.2 g of silica gel-supported sulfate-bound zirconium oxide catalyst (as prepared in Example 13) were thoroughly mixed and placed in the reactor tube (one inch diameter) of a recirculating loop reactor. The reactor tube was purged with $N_2$ and evacuated three times. The reactor tube was left under 15 p.s.i.g. of $N_2$. The reactor tube was heated to about 80° C. Ethylene oxide was charged to the reactor tube based on the following schedule:

| Reactor Time, Mins. | Reactor Temp., °C.[1] | Reactor Pressure, p.s.i.g. | Total Ethylene Oxide Feed, grams |
|---|---|---|---|
| 0 | 80°/82° | 19/32 | 5.1 |
| 5 | 78°/97° | 22/40 | 8.1 |
| 9 | 75°/98° | 22/40 | 10.7 |
| 13 | 70°/82° | 22/42 | 12.1 |
| 18 | 80°/78° | 22/42 | 13.4 |
| 22 | 78°/73° | 22/43 | 14.7 |
| 26 | 78°/74° | 22/45 | 16.2 |
| 31 | 79°/73° | 22/45 | 17.4 |
| 36 | 72°/70° | 22/45 | 18.7 |
| 41 | 77°/68° | 22/45 | 20.1 |
| 46 | 80°/68° | 22/42 | 21.5 |
| 52 | 85°/67° | 22/52 | 24.2 |
| 57 | 76°/72° | 24/52 | 29.7 |
| 63 | 80°/79° | 24/56 | 35.6 |
| 79 | 78°/76° | 24/55 | 43.3 |
| 84 | 80°/69° | 23/55 | 50.9 |
| 92 | 79°/69° | 24/54 | 58.6 |
| 102 | 83°/76° | 26/55 | 65.5 |
| 116 | 83°/71° | 26/55 | 72.1 |
| 127 | 80°/70° | 25/55 | 80.3 |
| 142[2] | 81°/69° | 28 | |
| 142 | 15° | 22 | |
| 174 | 85°/60° | 28/58 | 85.1 |
| 195 | 83°/67° | 30/58 | 90.0 |

-continued

| Time, Mins. | Reactor Temp., °C.[1] | Reactor Pressure, p.s.i.g. | Total Ethylene Oxide Feed, grams |
|---|---|---|---|
| 199 | 85°/64° | 30 | 91.9 |

Note:
[1] The first number is the temperature of the bomb, and the second number is the temperature inside of the reactor tube.
[2] Reactor shut down overnight and then restarted.

To samples taken during the run and the final product were analyzed by means of vapor phase chromatography. The product had a pH in water of neutral. The catalyst was washed with methanol to remove color caused by ethylene oxide. The product was CARBOWAX® polyethylene glycol produced by ethoxylation of ethylene glycol.

EXAMPLE 16

Preparation Of Sulfate-Bound Zirconium Oxide Catalyst 10 g of $Zr(OH)_4$ and 150 ml. of 0.5N $H_2SO_4$ were placed in a beaker and stirred for a few minutes. The solid was filtered off from the solution. The solid was calcined in a Pyrex tube at 575° C. (with air flow) for $3\frac{3}{4}$ hours. The calcined solid was white and had a pH in water of 1. The solid was stored in a desiccator until needed. The product was sulfate-bound zirconium oxide catalyst.

EXAMPLE 17

Ethoxylation Of 2-Octanol Using Sulfate-Bound Zirconium Oxide Catalyst 49.9 g of 2-octanol and 3.0 g of sulfate-bound zirconium oxyide catalyst (as prepared by the method of Example 16) were charged to a Parr bomb. The bomb was purged with $N_2$ and evacuated three times. The bomb was left under 15 p.s.i.g. of $N_2$. The bomb was heated and stirred vigorously. Ethylene oxide was added to the bomb based on the following schedule:

TABLE X

| Time Mins. | Reactor temp., °C. | Reactor Pressure, p.s.i.g. | Total Ethylene Oxide Feed, grams |
|---|---|---|---|
| 0 | 82° | 18/36 | 6.6 |
| 7 | 1 | 30 | |
| 11 | 115° | 31/54 | 11.4 |
| 19 | 112° | 31.58 | 17.0 |
| 44 | 108° | 33/52 | 20.2 |
| 52 | 107° | 48.49 | 20.5 |
| 113 | 107° | 26 | 20.5 |

Note: [1] The reactor temperature was increased to 100° C.

Immediately after the ethylene oxide was added to the bomb an exotherm to 85° C. occurred. At the 7 minute point in the run, the temperature of the reactor was increased to 110° C. and the reactor pressure rose to 31 p.s.i.g. When ethylene oxide was added at the 11 minute point in the run, an exotherm to 125° C. occurred. No noticeable exotherms occurred thereafter during the run. The product was analyzed using vapor phase chromatography. The product had a neutral pH in water.

The product was ethoxylates of 2-octanol.

EXAMPLE 18

Preparation Of Sulfate-Bound Zirconium Oxide 50 g of commercial $Zr(OH)_4$ (slightly damp, file white powder, with $NH_3$ odor) was washed free of $NH_3$ with distilled $H_2O$. After the 750 ml. washing, the pH was neutral. The powder was washed with an additional 250 ml. of distilled $H_2O$. The pH was still neutral. A check of the wash water for Cl was negative ($AgNO_3$ test). The powder was dried overnight in oven at 100° C. in an open beaker. 29.61 g of fine white powder was removed after drying. No $NH_3$ odor was evident. The pH of the solid in $H_2O$ was neutral.

10 grams of the treated $Zr(OH)_4$ was treated with 150 ml. of $1NH_2SO_4$ in a beaker with stirring for 5 to 10 minutes. The solution was filtered on No. 42 filter paper. The solid filtrate was dried for 2.5 hours in an open beaker in a 100° C. oven. The pH of the filtrate in water was 3. The solid was calcined in a Pyrex tube at 575° C. (with air flow) for $2\frac{3}{4}$ hours. The pH of the calcined solid in water was 0 to 1. One liter of distilled water and the solid were stirred overnight in a beaker at room temperature. The slid was filtered off. The solid filtrate was calcined in a Pyrex tube at 575° C. (with air flow) for 3.5 hours. The calcined solid was white and had a pH in water of 1 to 2. The product was sulfate-bound zirconium oxide catalyst.

EXAMPLE 19

Preparation Of Phosphate-Bound Zirconium Oxide Catalyst 10 grams of the treated $Zr(OH)_4$ (prepared by the method of Example 18) was treated with 150 ml. of 1N $(NH_4)_2HPO_4$ solution in a beaker with stirring for 5 to 10 minutes. The solution was filtered on No. 42 filter paper. The solid filtrate was dried for 2.5 hours in an open beaker in a 100° C. oven. The pH of the filtrate in water was 8. The solid was calcined in a Pyrex tube at 575° C. (with air flow) for $2\frac{3}{4}$ hours. The pH of the calcined solid in water was 2. One liter of distilled water and the solid were stirred overnight in a beaker at room temperature. The solid was filtered off. The solid filtrate was calcined in a No. 5 Pyrex tube at 575° C. (with air flow) for 3.5 hours. The calcined solid was light yellow and had a pH in water of 3 to 4. The zirconium oxy-anion product was phosphate-bound zirconium oxide catalyst.

EXAMPLE 20

Preparation Of Fluoride-Bound Zirconium Oxide Catalyst 9.61 grams of the treated $Zr(OH)_4$ was treated with 150 ml. of 1N HF solution in a beaker with stirring for 5 to 10 minutes. The solution was filtered on No. 42 filter paper. The solid filtrate was dried for 2.5 hours in an open beaker in a 100° C. oven. The pH of the filtrate in water was 4. The solid was calcined in a Pyrex tube at 575° C. (with air flow) for $2\frac{3}{4}$ hours. One liter of distilled water and the solid were stirred overnight in a beaker at room temperature. The solid was filtered off. The solid filtrate was calcined in a Pyrex tube at 575° C. (with air flow) for 3.5 hours. The calcined solid was pinkish and had a pH in water of 4, and was stored in a desiccator until needed. The product was fluoride-bound zirconium oxide catalyst.

EXAMPLE 21

Preparation Of CARBOWAX® Polyethylene Glycol Using Phosphate-Bound Zirconium Oxide Catalyst 51.3 g of ethylene glycol and 5.0 g of phosphate-bound zirconium oxide catalyst (prepared by the method of Example 19) were charged to a Parr bomb. The pH of the mixture was 5. (The pH of ethylene glycol by itself was 6.) The following formula was used to determine the amount of ethylene oxide needed:

$$\frac{\text{Wt. Of Starting Compound} \times \text{M.W. of Product}}{\text{Wt. Of Starting Compound}} =$$

$$\frac{\text{Wt. of Product} - \text{Wt. Of Starting Compound}}{\text{Wt. Of Ethylene Oxide}}$$

$$\frac{51.30 \text{ g} \times 200}{62.07 \text{ g}} = \frac{165.30 \text{ g (Product)} - 51.30 \text{ g}}{Y}$$

Y = 114.0 g of Ethylene Oxide

The bomb was purged with $N_2$ and evacuated three times. The bomb was left under 16 p.s.i.g. of $N_2$. The bomb was heated to 80° C. and stirred vigorously. Ethylene oxide was charged to the bomb based on the following schedule:

TABLE XI

| Time, Mins. | Reactor Temp., °C. | Reactor Pressure, p.s.i.g. | Total Ethylene Feed, Grams |
|---|---|---|---|
| 0 | 77° | 19/28 | 38 |
| 5 | 79° | 23/38 | 8.2 |
| 8 | 88° | 32/45 | 12.2 |
| 9 | 91° | 40/47 | 14.3 |
| 10 | 91° | 40/47 | 16.1 |
| 12 | 89° | 40/47 | 18.1 |
| 14 | 86° | 40/46 | 19.6 |
| 16 | 82° | 40/46 | 21.7 |
| 17 | 78° | 40/46 | 23.5 |
| 20 | 83° | 40/46 | 24.9 |
| 23 | 82° | 40/46 | 26.8 |
| 25 | 78° | 40/46 | 28.1 |
| 28 | 83° | 40 | 40.1[3] |
| 59 | 83° | 43 | [3] |
| 59 | 81° | 26/44 | 46.1 |
| 61 | 83° | 40/50 | 50.0[3] |
| 76 | [2] | 44 | |
| 81 | 126° | 40/57 | 51.9 |
| 84 | 130° | 40 | [3] |
| 246 | 122° | 54 | 97.0 |
| 314 | 122° | 51/56 | 97.8 |
| 324 | 121° | 51/58 | 98.7 |
| 338 | 121° | 51/64 | 99.7 |
| 356 | 122° | 52 | 100.8 |
| 364 | 122° | 52/72 | 102.4 |
| 378 | 122° | 54/72 | 103.7 |
| 394 | 121° | 54/72 | 104.6 |
| 414 | 122° | 54/72 | 107.0 |
| 438 | 122° | 54/64 | 105.0 |
| 439 | 121° | 55/76 | 109.4 |
| 454 | 121° | 56/74 | 112.3 |
| 484 | 121° | 56/80 | 114.7 |
| 504 | 121° | 60 | |
| [4] | 17° | 38 | |

Note:
[1] Turned off reactor heat and restarted the next day.
[2] The reactor temperature was increased to 125° C.
[3] Constant feed of ethylene oxide to the reactor and then the periodic addition was resumed as indicated.
[4] The reaction heat was cut and the ingredients were allowed to set overnight in the sealed bomb.

The reaction proceeded rapidly and an exotherm of 4° to 10° C. was observed on the first few additions. The rate of reaction slowed somewhat as ethylene oxide was added, but still was fairly rapid; and pressure built up somewhat (some due to volume effect). The bomb was allowed to set overnight at room temperature after 40.1 g of ethylene oxide had been added. The reaction was started at about 120° C. the following morning, and exotherm again was observed, as well as good activity. (A slow constant feed was tried at a couple points during the reaction with good results—fairly stable pressure.) The pressure built up eventually, so the constant feed was stopped (ethylene oxide was not consumed rapidly enough). Addition of ethylene oxide was difficult at the end of reaction due to high reactor pressure (higher than the feed). The liquid product was clear and colorless, and had a pH of 6. The catalyst was filtered out using No. 1 filter paper and then an F sintered glass funnel. The product was analyzed using vapor phase chromatography. The catalyst was rinsed out of the bottom of the bomb with about 100 ml. of distilled water. The pH of the wash water was 6 and the pH of the catalyst was 5. The catalyst was light brown. The catalyst was calcined in a Pyrex tube at 575° C. (with air flow) for 1 hour and then stored in a desiccator. The pH of the calcined catalyst in water was 2 to 3. The product was CARBOWAX® polyethylene glycol 200 prepared by the ethoxylation of ethylene glycol.

EXAMPLE 22

Preparation Of CARBOWAX® Polyethylene Glycol 200 Using Phosphate-Bound Zirconium Oxide Catalyst 50.8 g of ethylene glycol and 4.56 g of phosphate-bound zirconium oxide catalyst (which had been recovered and recalcined in Example 20) were charged to a Parr bomb. The pH of the mixture was 5. (The pH of ethylene glycol by itself was 6.) The following calculation determined the amount of ethylene oxide needed:

$$\frac{50.8 \times 200)}{62.07 \text{ g}} = \frac{163.69 \text{ g (product)} - 50.80 \text{ g}}{Y}$$

Y = 112.89 g of Ethylene Oxide

The bomb was purged with $N_2$ and evacuated three times.

The bomb was left under 16 p.s.i.g. of $N_2$. The bomb was heated to 120° C., stirred vigorously. Ethylene oxide was charged to the bomb based on the following schedule:

TABLE XII

| Time, Mins. | Reactor Temp., °C. | Reactor Pressure, p.s.i.g. | Total Oxide Feed, grams | Top Of Exotherm, °C. |
|---|---|---|---|---|
| 0 | 126° | 24/54 | 5.4 | 135° C. |
| 5 | 120° | 26/58 | 9.8 | 131° |
| 9 | 121° | 28/58 | 13.6 | 130° |
| 13 | 121° | 28/60 | 18.0 | 131° |
| 18 | 120° | 28/60 | 21.5 | 130° |
| 24 | 119° | 29/60 | 24.8 | 132° |
| 30 | 121° | 30/62 | 27.6 | 129° |
| 34 | 120° | 31/60 | 30.1 | 125° |
| 38 | 120° | 32/64 | 32.7 | 126° |
| 43 | 19° | 32[1] | | |
| 136 | 121° | 56[2] | 77.4 | |
| 225 | 120° | 46[3] | | |
| 267 | 121° | 56 | 84.0 | |
| 282 | 120° | 49/56 | 85.0 | |
| 305 | 120° | 49/60 | 86.1 | |
| 312 | 120° | 51/62 | 87.4 | |
| 318 | 120° | 54/66 | 88.3 | |
| 332 | 120° | 50/68 | 89.5 | |
| 355 | 121° | 50/62 | 90.8 | |
| 367 | 120° | 51/66 | 92.2 | |
| 373 | 120° | 55/66 | 93.1 | |
| 403 | 120° | 52/65 | 94.1 | |
| 415 | 121° | 52/66 | 95.3 | |
| 420 | 120° | 55/66 | 95.8 | |
| 445 | 120° | 52[4] | | |
| 445 | 18° | 36[5] | | |
| 447 | 128° | 51/60 | 99.5 | |

TABLE XII-continued

| Time, Mins. | Reactor Temp., °C. | Reactor Pressure, p.s.i.g. | Total Oxide Feed, grams | Top Of Exotherm, °C. |
|---|---|---|---|---|
| 448[6] | 121° | 54/60 | 99.7 | |

Notes:
[1]Started constant feed of ethylene oxide.
[2]Stopped constant feed of ethylene oxide.
[3]Resumed making ethylene oxide additions.
[4]Shut off reactor heat and allowed to set overnight.
[5]Resumed heating reactor.
[6]Run was shut down shortly thereafter.

The reaction was started at about 120° C. An exotherm was observed when ethylene oxide was added and the reaction rate was readily comparable to Example 21.

Exotherms continued for several additions of ethylene oxide. After 38 minutes of the run, a constant feeding of ethylene oxide at a rate of 1 g per 1.5 minutes was conducted. The reactor pressure at the start of the constant feed was 43 p.s.i. The reaction slowed as the total ethylene oxide feed approached 80 g. The feed rate had to be slowed as the pressure built up. The same happening had been observed in Example 21. It was not clear whether the slow down of the activity was due to catalyst inactivity, dilution effect (increased volume of liquid vs. fixed amount of catalyst), or high bomb pressure. The liquid product was clear and colorless and had a pH of 6. The liquid product was poured from the bomb. The product was analyzed using vapor phase chromatography. CARBOWAX ® polyethylene glycol 200 was not quite produced because not quite enough ethylene oxide was added. The purpose of this example is to see if the recovered and recalcined catalyst could be used to produce CARBOWAX ® ethylene glycol 200.

EXAMPLE 23

Preparation Of CARBOWAX ® Polyethylene Glycol 400 Using Sulfate-Bound Zirconium Oxide Catalyst 42.0 g of CARBOWAX ® polyethylene glycol 200 and 3.81 g of sulfate-bound zirconium oxide catalyst were charged to a Parr bomb. The bomb was purged with $N_2$ and evacuated three times. The bomb was left under 16 p.s.i.g. of $N_2$. The bomb was heated to 65° C. and stirred vigorously. The catalyst used in this reaction was less acidic than others used in some of these examples. Also the starting reaction was a lower temperature to try to eliminate high exotherms and possible color problems. Ethylene oxide was charged to the bomb based on the following schedule:

TABLE XIII

| Time, Mins. | Reactor Temp., °C. | Reactor Pressure, p.s.i.g. | Total Ethylene Oxide Feed, grams |
|---|---|---|---|
| 0 | 65° | 19/37 | 6.3 |
| 8 | 65° | 32/43 | 9.9 |
| 18 | 62° | 40 (1) | |
| 37 | 129° | 34/50 | 12.5 |
| 43 | 118° | 36/52 | 15.2 |
| 54 | 120° | 36/52 | 18.0 |
| 61 | 119° | 36/53 | 20.4 |
| 69 | 120° | 38/55 | 22.9 |
| 80 | 120° | 39/55 | 23.0 |
| 89 | 120° | 39/56 | 27.4 |
| 100 | 120° | 40 (2) | |
| 100 | 18° | 19 (3) | |
| 116 | 65° | 22/35 | 32.8 |
| 121 | 55 | 34 | |
| 138 | 129° | 52 (4) | |
| 145 | 122° | 40/58 | 34.2 |

TABLE XIII-continued

| Time, Mins. | Reactor Temp., °C. | Reactor Pressure, p.s.i.g. | Total Ethylene Oxide Feed, grams |
|---|---|---|---|
| 151 | 124° | 40/58 | 35.9 |
| 155 | 131° | 40/58 | 37.7 |
| 172 | 125° | 40/70 | 39.4 |
| 183 | 121° | 38/68 | 40.8 |
| 193 | 124° | 40/58 | 42.0 |
| 230 | 123° | 36 (5) | |
| 260 | 31° | 22 | |

Notes:
(1) Reactor temperature was raised to about 120° C.
(2) Reactor was shut down overnight.
(3) Reactor was restarted.
(4) Temperature was raised to about 120° C.
(5) The heat was turned off.

There was very little exotherm on the initial ethylene oxide addition. Also, the reaction was slow at 65° C., so the temperature was raised to about 120° C. The reaction rate was much faster, but still no exotherm was observed when ethylene oxide was added. The reaction was stopped overnight. At that point, the liquid product was clear and colorless, and had a pH of 6. The reaction restarted at 65° C. to try to avoid high temperature operation and possible decomposition. After adding a small amount of ethylene oxide, the temperature was raised to about 120° C. (At one point in the run, the temperature reached 135° to 136° C. for about 5 minutes.) After the initial slight exotherm, no further exotherms were detected. The reaction was slow toward the end. The reaction was stopped and the gaseous ethylene oxide was removed. The liquid product was light yellow and had a pH of 6. The (pinkish brown) catalyst was filtered off. The catalyst was washed with 150 ml of distilled water, which resulted in a white catalyst. The pH of the water was 3 to 4 and of the catalyst in the water was 3. The catalyst was light yellow in water and was white when dry. The molecular weight of the product was too high and possibly the gas chromatography column might be plugged, so no vapor phase chromatography analysis was made. The catalyst was calcined in a Pyrex tube at 575° C. (with air flow) for 3.5 hours.

EXAMPLE 24

Hydrolysis Of Ethylene Oxide Using Sulfate-Bound Zirconium Oxide Catalyst 40.0 g of water and 3.30 g of sulfate-bound zirconium oxide catalyst (the recovered, recalcined catalyst from Example 23) were charged to a Parr bomb. The bomb was purged with $N_2$ and evacuated three times. The bomb was left under 16 p.s.i.g. of $N_2$. The bomb was hated to about 80° C. and stirred vigorously. Ethylene oxide was charged to the bomb based on the following schedule:

TABLE XIV

| Time, Mins. | Reactor Temp., °C. | Reactor Pressure p.s.i.g. | Total Ethylene Oxide Feed, grams |
|---|---|---|---|
| 0 | 78° | 22/38 | 3.3 |
| 10 | 79° | 31/42 | 6.0 |
| 24 | 78° | 26/43 | 9.3 |
| 35 | 79° | 29/44 | 13.4 |
| 55 | 79° | 26 (1) | |
| | 18° | 17 (2) | |
| 55 | 102° | 30/54 | 17.6 |
| 58 | 100° | 34/50 | 19.9 |
| 62 | 105° | 38/58 | 21.6 |
| 64 | 106° | 38/56 | 23.1 |

TABLE XIV-continued

| Time, Mins. | Reactor Temp., °C. | Reactor Pressure p.s.i.g. | Total Ethylene Oxide Feed, grams |
|---|---|---|---|
| 66 | 105° | 38/58 | 24.1 |
| 68 | 104° | 38/54 | 26.6 |
| 72 | 103° | 38/58 | 28.2 |
| 74 | 104° | 38/56 | 30.1 |
| 78 | 103° | 38/58 | 32.0 |
| 82 | 105° | 38/58 | 34.0 |
| 85 | 102° | 38/58 | 35.5 |
| 88 | 101° | 38/58 | 37.0 |
| 91 | 99° | 38/59 | 38.9 |
| 94 | 100° | 38/59 | 41.2 |
| 99 | 100° | 38/59 | 43.2 |
| 103 | 99° | 38/59 | 45.3 |
| 105 | 99° | 38/58 | 46.9 |
| 109 | 99° | 38/59 | 49.0 |

Notes
(1) Heat was turned off overnight.
(2) Heat was applied again next day.

No exotherms were observed until the temperature was raised to about 100° C. Small exotherms (2° to 5° C.) were observed thereafter when ethylene oxide was added. The rate of reaction was faster at 100° C., and remained fairly fast throughout the reaction. The reaction was stopped, the bomb was evacuated and the catalyst was filtered out. The liquid product was clear and colorless, although some of the catalyst remained in the product. The product had a pH of 4 to 5. 25.56 g of water was removed from the product on a Rotavapor at 90° C. and 30 inches of vacuum. 20.54 g of product remained as a kettle product. 75 ml of ethyl acetate was added to the kettle product in a separation funnel but layers were evident. The material was removed and dried over anhydrous $MgSO_4$ (no clumping was observed). The solution was filtered and the ethyl acetate was removed in vacuo from the solid filtrate. The solid product was analyzed using vapor phase chromatography. The product was hydrolyzed ethylene oxide (ethylene glycol, diethylene glycol, and triethylene glycol).

EXAMPLE 25

Ethoxylation Of 1-Butanol Using Sulfate-Bound Zirconium Oxide Catalyst 74.1 g (1 mole) of 1-butanol nd 3.30 g of sulfate-bound zirconium oxide catalyst were charged to a Parr bomb. (The catalyst had been prepared by the procedure of Example 1.) The bomb was purged with $N_2$ and evacuated three times. The bomb was left under 16 p.s.i.g. of $N_2$. The bomb was heated to about 100° C. and stirred vigorously. The pH of the material in the bomb was 6. Ethylene oxide was charged to the bomb based on the following schedule:

TABLE XV

| Time, Mins. | Reactor Temp., °C. | Reactor Pressure p.s.i.g. | Total Ethylene Oxide Feed, grams |
|---|---|---|---|
| 0 | 112° | 24/33 | 5.5 |
| 17 | 110° | 33/42 | 8.7 |
| 33 | 109° | 34/42 | 11.0 |
| 136 | 109° | 27 | |

Once ethylene oxide was added, the reaction proceeded slowly. The reaction was kept at 109° C. for two hours after the last ethylene oxide addition, and then the reactor system was shut down. A total of 11 grams of ethylene oxide were used, so the molar ratio of 1-butanol to ethylene oxide was 4 to 1. The product was clear and colorless and had a pH of 6. The catalyst was filtered off. The catalyst was placed in a Pyrex tube and calcined at 575° C. (with air flow) for 3.5 hours. The pH of the catalyst in water was neutral. The product was ethoxylates of 1-butanol.

EXAMPLE 26

Ethoxylation Of 1-Butanol Using Sulfate-Bound Zirconium Oxide Catalyst 74.1 g (1 mole) of 1-butanol and 5.20 g of sulfate-bound zirconium oxide catalyst (which had been recovered and recalcined in Example 25) were charged to a Parr bomb. The bomb was purged with $N_2$ and evacuated three times. The bomb was left under 16 p.s.i.g. of $N_2$. The bomb was heated to 80° C. and stirred vigorously. The pH of the material in the bomb was 6. Ethylene oxide was charged to the bomb based on the following schedule:

TABLE XVI

| Time, Mins. | Reactor Temp., °C. | Reactor Pressure p.s.i.g. | Total Ethylene Oxide Feed, grams |
|---|---|---|---|
| 0 | 81° | 19/33 | 6.6 |
| 7 | (1) | 32 | |
| 10 | 110° | 40/45 | 9.8 |
| 15 | 108° | 40/46 | 11.1 |
| 80 | | 29 | |

Note:
(1) Raised temperature of the reactor.

Once ethylene oxide was added, the reaction proceeded slowly and no exotherm was noticed. So the temperature was raised to 110° C. and the reaction rate increased. No exotherms were noticed at the higher temperature level. The reactor system was shut down. A total of 11.1 g of ethylene oxide were used, so the molar ratio of 1-butanol to ethylene oxide was 4 to 1. The liquid product was clear and colorless and had a pH of 6. The catalyst was filtered off. The product was analyzed by vapor phase chromatography. The excess catalyst was rinsed (but not washed) from the bomb using acetone. The catalyst was calcined in a Pyrex tube at 575° C. (with air flow) for 3 hours. The pH of the calcined catalyst was neutral. The product was ethoxylates of 1-butanol.

EXAMPLE 27

Ethoxylation Of Glycerol Using Sulfate-Bound Zirconium Oxide Catalyst 60.2 g of anhydrous glycerol and 3.0 g of sulfate-bound zirconium oxide catalyst were charged to a Parr bomb. (The catalyst had been prepared by the procedure of Example 1.) The bomb was purged with $N_2$ and evacuated three times. The bomb was left under 16 p.s.i.g. of $N_2$. The bomb was heated to 80° C. and stirred vigorously. The pH of the material in the bomb was 5 to 6. Ethylene oxide was charged to the bomb based on the following schedule:

TABLE XVII

| Time, Mins. | Reactor Temp., °C. | Reactor Pressure, p.s.i.g. | Total Ethylene Oxide Feed, grams | Top Of Exotherm, °C. |
|---|---|---|---|---|
| 0 | 81° | 18/57 | 3.4 | 86° |
| 6 | 80° | 36/58 | 6.7 | 86° |
| 13 | 79° | 42/56 | 9.3 | 86° |
| 15 | 78° | 44/56 | 11.7 | 87° |
| 26 | 78° | 42/56 | 14.2 | 89° |
| 35 | 80° | 40/54 | 17.3 | 83° |

TABLE XVII-continued

| Time, Mins. | Reactor Temp., °C. | Reactor Pressure, p.s.i.g. | Total Ethylene Oxide Feed, grams | Top Of Exotherm, °C. |
|---|---|---|---|---|
| 40 | 82° | 44/54 | 19.6 | |
| 59 | 80° | 29/47 | 22.0 | |
| 107 | 81° | 24 | | |

A small exotherm (about 6° C.) was observed for the first few additions of ethylene oxide. The reaction rate was slower than with ethylene glycol, but it still was fairly fast. The liquid product was clear and colorless, and had a pH of 5. The catalyst was filtered off, but the filtration was very difficult because the liquid product was very thick (viscous). The product was analyzed by vapor phase chromatography. The catalyst was washed with about 200 ml of distilled water and placed in a test tube. The product was ethoxylated glycerol.

EXAMPLE 28

Ethoxylation Of 1-Butanol Using Sulfate-Bound Zirconium Oxide Catalyst 74.1 g (1 mole) of 1-butanol and 3.0 g of sulfate-bound zirconium oxide catalyst were charged to a Parr bomb. (The catalyst had been prepared by procedure of Example 1.) The bomb was purged with $N_2$ and evacuated three times. The bomb was left under 16 p.s.i.g. of $N_2$. The bomb was heated to 110° C. and stirred vigorously. The pH of the material in the bomb was 5 to 6. Ethylene oxide was charged to the bomb based on the following schedule:

TABLE XVIII

| Time, Mins. | Reactor Temp., °C. | Reactor Pressure, p.s.i.g. | Total Ethylene Oxide Pressure, grams |
|---|---|---|---|
| 0 | 110° | 22/32 | 5.3 |
| 15 | 110° | 32/40 | 8.4 |
| 31 | 109° | 33/42 | 11.2 |
| 50 | 109° | 27 | |

The reaction rate was fairly slow but was comparable with other 1-butanol runs. The reactor was shut down, and the catalyst was filtered out of the liquid product. 79.52 g of the liquid product was obtained. A total of 11.2 g of ethylene oxide was used, so the molar ratio of 1-butanol to ethylene oxide was 4 to 1. The liquid product was clear and colorless and had a pH of 5 to 6. The liquid product was analyzed by vapor phase chromatography.

40 g of the liquid product was distilled in the fractionating column having a small condenser. The fractions of the distillation were:

TABLE XIX

| Fraction | Temp., °C. | Wt. g. | Percent Of Total Product |
|---|---|---|---|
| 1-Butanol | 117° | 27.39 | 69.4 |
| Butyl Cellosolve ™ | 171° | 7.46 | 18.9 |
| Kettle Product (higher ethoxylates) | | 4.61 | 11.7 |
| Total | | 39.46 | 100 |

28.71 g of the liquid product was separated into 1-butanol and butyl cellosolve on a Rotavapor. (conditions: 60° C. on water bath, vacuum pump on condensor). The fractions were:

TABLE XX

| Receiver | Wt., g[1] | Percent Of Total Product |
|---|---|---|
| Butanol | 16.90 | 65.5 |
| Kettle Product Butyl Cellosolve ™ Higher Ethoxylates | 8.92 | 34.5 |
| Total | 25.82 | 100 |

Note:
[1] Probably lost some product to the vacuum.

EXAMPLE 29

Calcining Commercial Zirconium Sulfate Oxide

Commercial zirconium sulfate oxide was placed in a Pyrex tube and calcined at 800° C. (with air flow) for $2\frac{3}{4}$ hours. The pH of the catalyst after calcining was 2. The calcined catalyst was insoluble in water.

EXAMPLE 30

Preparation Of CARBOWAX ® Polyethylene Glycol Using Calcined Commercial Zirconium Sulfate Oxide 40.0 g of ethylene glycol and 2.5 g of the calcined commercial zirconium sulfate oxide from Example 29 were charged to a Parr bomb. The formula for commercial zirconium sulfate oxide is $ZrO(SO_4).H_2SO_4.3H_2O$. The bomb was purged with $N_2$ and evacuated three times. The bomb was left under 16 p.s.i.g. of $N_2$. The bomb was heated to 80° C. and stirred vigorously. The pH of the material in the bomb was 5. Ethylene oxide was charged to the bomb based on the following schedule:

TABLE XXI

| Time, Mins. | Reactor Temp., °C. | Reactor Pressure, p.s.i.g. | Total Ethylene Oxide Feed, grams | Top Of Exotherm, °C. |
|---|---|---|---|---|
| 0 | 79° | 18/32 | 5.0 | 91° |
| 7 | 83° | 24/44 | 11.4 | 106° |
| 11 | 79° | 25/40 | 16.3 | 87° |
| 18 | 82° | 30/46 | 22.1 | (1) |
| 27 | 81° | 28/46 | 29.5 | |
| 66 | 80° | 24/44 | 35.2 | 85° |
| 76 | 83° | 38/54 | 40.0 | |
| 109 | 83° | 38 | | |

Note:
(1) No exotherm was noticed.

Exotherms were observed upon the first few additions of ethylene oxide. The reaction rate was slower than the sulfate-bound zirconium oxide catalysts prepared in the above examples, but it was still fairly fast. The reactor was shut down and the catalyst was filtered from the liquid product. The liquid product was clear and colorless, and had a pH of 5 to 6. The product was analyzed by vapor phase chromatography. Catalyst was rinsed from the bomb. The catalyst was calcined in a Pyrex tube at 575° C. (with air flow) for 1 hour. 2.05 g of catalyst was recovered. The pH of the catalyst in water was about 6. The product was CARBOWAX ® polyethylene glycol prepared by the ethoxylation of ethylene glycol.

EXAMPLE 31

Preparation of Sulfuric Acid-Treated Zirsil 401 Catalyst

Zirsil 401 (from Magnesium Elektron, Inc.) was dried at 100° C. in an open beaker over a weekend. 25 g. of the dried white powder was treated with 375 ml. of 1N $H_2SO_4$ in a beaker with stirring for about 5 minutes. The admixture was filtered. The solid filtrate was dried at 100° for 1.5 hours. The solid was calcined in Pyrex tubes at 575° C. (with air flow) for 2 hours. Zirisil 401 is a composition which includes 52 percent of silicon oxide, 16 percent of hydrous zirconium oxide, 12 percent of zircon, 2 to 3 percent of sodium iron at 120 ppm and titanium at 150 ppm, which has an ignition loss at 1000° C. for one hour of 20 percent (mostly water), and which has a free moisture at 150° C. for 15 minutes of 12 percent.

EXAMPLE 32

Preparation Of Basic Sulfate-Bound Zirconium Oxide Catalyst 35.0 g of basic sulfate-bound zirconium oxide (which had a pH of 2 in water) was placed in a crucible with the lid ajar and was calcined at 800° C. (with air flow) for 3 hours. The pH of the catalyst in water was 3.

EXAMPLE 33

Treatment Of Sulfate-Bound Zirconium Oxide Catalyst With Sodium Hydroxide 3.85 g of sulfate-bound zirconium oxide catalyst (which had a pH of 2 in water) was treated with 50 ml of 0.5N NaOH solution in a beaker with stirring for about 1 minute. (The catalyst had been prepared by the procedure of Example 1.) The admixture was filtered. The solid filtrate was calcined in a Pyrex tube at 575° C. (with air flow) for 1 hour. The pH of the calcined catalyst in water was 9.

EXAMPLE 34

Preparation of CARBOWAX ® Polyethylene Glycol Using Basic Sulfate-Bound Zirconium Oxide Catalyst 40.1 g of ethylene glycol and 5.0 g of the basic sulfate-bound zirconium oxide catalyst of Example 33 were charged to a Parr bomb. The bomb was purged with $N_2$ and evacuated three times. The bomb was left under 16 p.s.i.g. of $N_2$. The bomb was heated about 85° C. and stirred vigorously. The pH of the material in the bomb was 5 to 6. Ethylene oxide was charged to the bomb based on the following schedule:

TABLE XXII

| Time, Mins. | Reactor Temp., °C. | Reactor Pressure p.s.i.g. | Total Ethylene Oxide Feed, grams |
|---|---|---|---|
| 0 | 85° | 18/46 | 5.9 |
| 25 | 105° | 23/54 | 9.5 |
| 43 | 110° | 24/56 | 13.8 |
| 63 | 112° | 25/50 | 16.7 |
| 73 | 110° | 30/58 | 19.1 |
| 85 | 112° | 32/54 | 20.6 |
| 98 | 111° | 28/58 | 22.7 |
| 106 | 111° | 33 (1) | |
| 106 | 115° | 25/54 | 27.4 |
| 151 | 110° | 27/64 | 31.5 |
| 206 | 110° | 28/62 | 35.5 |
| 247 | 110° | 33/68 | 40.5 |

TABLE XXII-continued

| Time, Mins. | Reactor Temp., °C. | Reactor Pressure p.s.i.g. | Total Ethylene Oxide Feed, grams |
|---|---|---|---|
| 406 | 108° | 30 | |

Note:
(1) The reactor heat was cut off and the reactor sat overnight.

No exotherm was noticed after the first ethylene oxide addition. After the second ethylene oxide addition, there was an exotherm to 123° C. but there was no reaction after 5 minutes because there was no pressure drop. The pressure was increased to 110° C. and there was an exotherm to 114° C. The reactor was shut down after the run. The catalyst was filtered out of the liquid product and placed in a test tube.

EXAMPLE 35

Hydrolysis Of Zirconyl Acetate To Produce Sulfate-Bound Zirconium Oxide Catalyst 30 g of $(NH_4)_2SO_4$ were dissolved in 100 ml of distilled water. 11.26 g of zirconyl acetate, i.e., ZrO(OAc)$_2$ where OAc is $C_2H_3O_2$, was added to the solution. An additional 50 ml of distilled water was added. At this point, the pH of the solution was 4 to 5. A total of 9.5 ml of 4M NaOH was added to the solution to raise the pH to 9. The solid material was filtered out of the solution and washed with acetone. The solid was calcined in Pyrex tubes at 575° C. (with air flow) for 3.5 hours. The pH of the calcined solid in water was 1. 2 grams of the calcined material was set aside for later use. The remainder of the calcined material was washed with about 200 ml of distilled water and then rinsed with acetone to dry it. The material was then calcined in a Pyrex tube at 520° C. (with air flow) for 23 hours. The pH of the solid in water was 1 to 2. The solid was sulfate-bound zirconium oxide catalyst.

EXAMPLE 36

Preparation of CARBOWAX ® Polyethylene Glycol Using Sulfate-Bound Zirconium Oxide Catalyst 40.0 g of ethylene glycol and 2.0 g of sulfate-bound zirconium oxide catalyst (that which was set aside in Example 35 for a later use) were charged to a Parr bomb. The bomb was purged with $N_2$ and evacuated three times. The bomb was left under 16 p.s.i.g. of $N_2$. The bomb was heated to about 80° C. and stirred vigorously. The pH of the material in the bomb initially was 5, but the pH stick slowly changed to 2. Ethylene oxide was charged to the bomb based on the following schedule:

TABLE XXIII

| Time, Mins. | Reactor Temp., °C. | Reactor Pressure, p.s.i.g. | Total Ethylene Oxide Feed, grams | Top Of Exotherm, °C. |
|---|---|---|---|---|
| 0 | 82° | 20/42 | 5.7 | 108° |
| 4 | 91° | 29/50 | 10.6 | (1) |
| 11 | 91° | 30/45 | 16.0 | (1) |
| 25 | 108° | 28/55 | 20.0 | 128° |
| 31 | 110° | 32/55 | 23.6 | 119° |
| 37 | 103° | 32/60 | 27.5 | 130°(1) |
| 47 | 112° | 34/60 | 30.2 | 124°(1) |
| 54 | 112° | 36/60 | 34.7 | 117°(1) |
| 67 | 109° | 34/60 | 40.0 | |
| 99 | 114° | 34 | | |

An exotherm was observed upon the first ethylene oxide addition, and the reaction rate was fairly fast. At the 25 minute addition, the reaction temperature was raised to about 110° C. Thereafter, mild exotherms occurred and the reaction rate remained fairly fast. After the reactor was closed down, the catalyst was filtered out of the liquid product and discarded. The pH of the liquid product was 5. The liquid product was analyzed using vapor phase chromatography. The CARBOWAX ® polyethylene glycol product contained a large amount of undesirable 1,4-dioxane.

EXAMPLE 37

Hydrolysis Of Hafnyl Chloride To Product Sulfate-Bound Hafnyl Oxide Catalyst 16.4 g of HfOCl$_2$.8H$_2$O were dissolved in 100 ml of distilled water. The pH of the solution was 0 to 1. Concentrated NH$_4$OH was added, with stirring, until the solution pH reached 9 and a white, gelatinous precipitate formed. 6 ml of NH$_4$OH were added to the solution, which was stirred for 10 minutes. The product precipitated out of the solution. The solid filtrate was washed overnight in a Soxhlet extractor with distilled water. The wash water in the Soxhlet extractor with the catalyst has a pH of 7 and was negative for Cl$^-$ (AgNO$_3$ test). The wash water in the flask has a pH of 7 and tested positive for Cl$^-$. The solid was dried in an open beaker set in an oven (100° to 120° C.) for about 24 hours. 7.05 g of solid was obtained. The solid was treated with 106 ml of 1NH$_2$SO$_4$ in a beaker with stirring for about 5 minutes. The solid was dried overnight at 110° to 120° C. The pH of the solid in water was 2. The solid was calcined in a Pyrex tube at 575° C. (with air flow) for 4.5 hours. The resultant fine white powder had a pH of 1 in water. The solid was sulfate-bound hafnyl oxide catalyst.

EXAMPLE 38

Preparation of CARBOWAX ® Polyethylene Glycol Using Sulfate-Bound Hafnyl Oxide Catalyst 40.0 g of ethylene glycol and 2.0 g of sulfate-bound hafnyl oxide catalyst (as prepared in Example 38) were charged to a Parr bomb. The bomb was purged with N$_2$ and evacuated three times. The bomb was left under 16 p.s.i.g. of N$_2$. The pH of the material in the bomb was 3 (and was slow to change). The bomb was heated to 100° C. and stirred vigorously. Ethylene oxide was added to the bomb based on the following schedule:

TABLE XXIV

| Time, Mins. | Reactor Temp., °C. | Reactor Pressure, p.s.i.g. | Total Ethylene Oxide Feed, grams | Top Of Exotherm, °C. |
|---|---|---|---|---|
| 0 | 100° | 21/46 | 5.4 | 134° |
| 3 | 110° | 28/50 | 10.2 | 136° |
| 5 | 111° | 29/50 | 15.1 | 135° |
| 8 | 111° | 30/50 | 20.2 | 135° |
| 10 | 111° | 30/50 | 25.3 | 130° |
| 13 | 109° | 32/50 | 30.1 | 124° |
| 16 | 109° | 33/50 | 33.0 | 116° |
| 20 | 111° | 33/50 | 35.4 | 115° |
| 23 | 110° | 34/52 | 37.7 | 113° |
| 25 | 109° | 35/50 | 40.0 | (1) |
| 49 | 110° | 35 | | |

Note:
(1) No exotherm.

The reaction was run at 100° to 110° C. Fairly large exotherms occurred run when ethylene oxide was added. The reaction rate was very fast (when compared to the fastest zirconium compound catalyst tested in the above examples). The catalyst was filtered from the product, and washed with about 25 ml of methanol. The catalyst was placed in a Pyrex test tube and placed in a 530° C. oven (with air flow) for about 12 days. The liquid product was analyzed using vapor phase chromatography. The product contained a fairly large amount of dioxane. The product was CARBOWAX ® polyethylene glycol produced by ethoxylation of ethylene glycol.

What is claimed is:

1. Process comprising reacting at least one molecule of a liquid or solid epoxide compound having the formula:

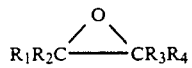

wherein R$_1$, R$_2$, R$_3$ and R$_4$ are each H or —(CH$_2$)$_n$CH$_3$, and wherein n is 0 to 3, with the proviso that R$_1$, R$_2$, R$_3$ and R$_4$ are the same or different, with at least one other molecule of said epoxide compound in the presence of catalytic amount of at least one solid anion-bound metal oxide heterogeneous catalyst, wherein said anion in said anion-bound metal oxide heterogeneous catalyst is SO$_4$, BF$_4$, CO$_3$, BO$_3$, HPO$_4$, SeO$_4$, MoO$_4$, B$_4$O$_7$ or PF$_6$, and the metal oxide is zirconium oxide, nickel oxide, aluminum oxide, tin oxide, magnesium oxide, iron oxide, titanium oxide, thorium oxide, hafnium oxide or rubidium oxide, said anion-bound metal oxide heterogeneous catalyst being an amorphous or primarily amorphous compound, and said molecules of said epoxide compound being the same epoxide compound or different epoxide compounds.

2. Process as claimed in claim 1 wherein 0.5 to 50 weight percent, based on the total weight of said epoxide compound, of said anion-bound metal oxide catalyst is used.

3. Process as claimed in claim 1 wherein said anion-bound metal oxide catalyst is an anion-bound zirconium oxide catalyst, an anion-bound nickel oxide catalyst, an anion-bound aluminum oxide catalyst, an anion-bound tin oxide catalyst, an anion-bound calcium oxide catalyst, an anion-bound magnesium oxide catalyst, an anion-bound rubidium oxide catalyst, an anion-bound titanium oxide catalyst, an anion-bound thorium oxide catalyst, an anion-bound hafnium oxide catalyst, or an anion-bound iron oxide catalyst.

4. Process as claimed in claim 1 wherein said catalyst is a solid anion-bound zirconium oxide catalyst.

5. Process as claimed in claim 4 wherein said solid anion-bound zirconium oxide catalyst contains about 2 to about 3 weight percent, based on the total weight of said catalyst, of said anion.

6. Process as claimed in claim 5 wherein said catalyst is an anion-bound thorium oxide catalyst.

7. Process as claimed in claim 1 wherein said catalyst is a solid sulfate-bound hafnium oxide catalyst.

8. Process as claimed in claim 1 wherein said catalyst is supported on an inert carrier.

9. Process as claimed in claim 1 wherein an inert liquid diluent is also present.

10. Process as claimed in claim 1 wherein the epoxide compound is ethylene oxide, or propylene oxide.

11. Process as claimed in claim 1 wherein said reaction is continuously conducted in a fluidized reactor.

12. Process as claimed in claim 1 wherein said anion-bound metal oxide is removed from the reaction site and is regenerated by calcination in air or oxygen at a temperature of 300° to 950° C. for a period of 1 to 4 hours.

* * * * *